US010449480B2

(12) United States Patent
Ji et al.

(10) Patent No.: US 10,449,480 B2
(45) Date of Patent: Oct. 22, 2019

(54) MEMBRANE AND PRESSURE SWING ADSORPTION HYBRID INRU PROCESS

(71) Applicant: Chevron Phillips Chemical Company LP, The Woodlands, TX (US)

(72) Inventors: Lei Ji, Kingwood, TX (US); Joseph A. Curren, Kingwood, TX (US); Ji Xian Loh, Houston, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 143 days.

(21) Appl. No.: 15/824,656

(22) Filed: Nov. 28, 2017

(65) Prior Publication Data

US 2018/0169563 A1 Jun. 21, 2018

Related U.S. Application Data

(60) Provisional application No. 62/434,832, filed on Dec. 15, 2016.

(51) Int. Cl.
*B01D 53/047* (2006.01)
*B01D 53/22* (2006.01)
(Continued)

(52) U.S. Cl.
CPC ......... *B01D 53/047* (2013.01); *B01D 53/002* (2013.01); *B01D 53/229* (2013.01);
(Continued)

(58) Field of Classification Search
CPC .... B01D 53/002; B01D 53/047; B01D 53/22; B01D 53/229; B01D 2256/24;
(Continued)

(56) References Cited

U.S. PATENT DOCUMENTS

| 3,248,179 A | 4/1966 | Norwood |
| 4,501,885 A | 2/1985 | Sherk et al. |

(Continued)

FOREIGN PATENT DOCUMENTS

| EP | 1024187 A1 | 8/2000 |
| EP | 1302233 A2 | 4/2003 |

(Continued)

OTHER PUBLICATIONS

Foreign communication from the corresponding International Application No. PCT/US2017/063474, International Search Report and Written Opinion, dated Feb. 16, 2018, 16 pages.

(Continued)

*Primary Examiner* — Frank M Lawrence, Jr.
(74) *Attorney, Agent, or Firm* — Conley Rose, P.C.

(57) ABSTRACT

A process for component separation in a polymer production system, comprising: separating a polymerization product stream into a gas stream and a polymer stream; contacting the polymer stream with a purge gas to yield a purged polymer stream and a spent purge gas stream; introducing the spent purge gas stream to a compressor to produce a compressed gas stream; introducing the compressed gas stream to a first separation unit to produce a first hydrocarbon stream and a membrane unit feed stream; introducing the membrane unit feed stream to a membrane unit to produce a first recovered purge gas stream and a retentate stream; introducing the retentate stream to a second separation unit to produce a second hydrocarbon stream and a PSA unit feed stream; and introducing the PSA unit feed stream to a PSA unit to produce a second recovered purge gas stream and a tail gas stream.

21 Claims, 5 Drawing Sheets

(51) Int. Cl.
*C07C 2/04* (2006.01)
*C07C 9/12* (2006.01)
*C08F 10/02* (2006.01)
*B01D 53/00* (2006.01)
*C07C 7/00* (2006.01)
*C07C 7/12* (2006.01)
*C07C 7/144* (2006.01)

(52) U.S. Cl.
CPC ............... *C07C 2/04* (2013.01); *C07C 7/005* (2013.01); *C07C 7/12* (2013.01); *C07C 7/144* (2013.01); *C07C 9/12* (2013.01); *C08F 10/02* (2013.01); *B01D 2256/24* (2013.01); *B01D 2257/102* (2013.01); *B01D 2257/7022* (2013.01); *B01D 2259/40001* (2013.01)

(58) Field of Classification Search
CPC ...... B01D 2257/102; B01D 2257/7022; B01D 2259/40001; C07C 9/12; C07C 7/005; C07C 7/12; C07C 7/144; C07C 2/04; C08F 10/02
USPC ............... 95/43, 47, 96, 130, 143, 144, 141; 585/802, 818, 820, 826
See application file for complete search history.

(56) References Cited

U.S. PATENT DOCUMENTS

| | | | |
|---|---|---|---|
| 4,588,790 A | 5/1986 | Jenkins, III et al. | |
| 5,352,749 A | 10/1994 | DeChellis et al. | |
| 5,436,304 A | 7/1995 | Griffin et al. | |
| 5,565,175 A | 10/1996 | Hottovy et al. | |
| 5,575,979 A | 11/1996 | Hanson | |
| 6,225,421 B1 | 5/2001 | Promel et al. | |
| 6,239,235 B1 | 5/2001 | Hottovy et al. | |
| 6,262,191 B1 | 7/2001 | Hottovy et al. | |
| 6,428,606 B1 | 8/2002 | Gottschlich et al. | |
| 6,706,857 B2 | 3/2004 | Golden et al. | |
| 6,833,415 B2 | 12/2004 | Kendrick et al. | |
| 7,163,906 B2 | 1/2007 | McDaniel et al. | |
| 7,449,048 B2 | 11/2008 | Nishida et al. | |
| 7,619,047 B2 | 11/2009 | Yang et al. | |
| 7,790,820 B2 | 9/2010 | Jensen et al. | |
| 7,960,487 B2 | 6/2011 | Yang et al. | |
| 8,138,113 B2 | 3/2012 | Yang et al. | |
| 8,207,280 B2 | 6/2012 | Murray et al. | |
| 8,268,944 B2 | 9/2012 | Yang et al. | |
| 8,450,436 B2 | 5/2013 | Masino et al. | |
| 9,108,891 B1* | 8/2015 | Ji ............................. | C07C 7/005 |
| 9,126,878 B1 | 9/2015 | Ji et al. | |
| 9,180,405 B2 | 11/2015 | Hottovy et al. | |
| 9,181,372 B2 | 11/2015 | Yang et al. | |
| 2001/0018499 A1 | 8/2001 | Marissal et al. | |
| 2003/0070546 A1* | 4/2003 | Zwilling .............. | B01D 53/047 95/96 |
| 2004/0136882 A1* | 7/2004 | Verser ................... | B01J 8/0015 422/132 |
| 2009/0208375 A1 | 8/2009 | Vandaele | |

FOREIGN PATENT DOCUMENTS

| | | |
|---|---|---|
| WO | 2006015807 A1 | 2/2006 |
| WO | 2016020042 A1 | 2/2016 |

OTHER PUBLICATIONS

Filing receipt and specification for provisional application entitled "Membrane and Pressure Swing Adsorption Hybrid INRU Process," by Lei Ji, et al., filed Dec. 15, 2016 as U.S. Appl. No. 62/434,832.

Filing receipt and specification for international application entitled "Membrane and Pressure Swing Adsorption Hybrid INRU Process," by Lei Ji, et al., filed Nov. 28, 2017 as serial No. PCT/US2017/063474.

McNaught, Alan D., et al., "Compendium of Chemical Terminology," IUPAC Recommendations, Second edition, 1997, 5 pages, Wiley-Blackwell.

* cited by examiner

MEMBRANE AND PRESSURE SWING ADSORPTION HYBRID INRU PROCESS

CROSS-REFERENCE TO RELATED APPLICATIONS

The present application is a non-provisional of and claims priority to U.S. Provisional Patent Application No. 62/434,832 filed Dec. 15, 2016 and entitled "Membrane and Pressure Swing Adsorption Hybrid INRU Process," which application is incorporated by reference herein in its entirety.

TECHNICAL FIELD

The present disclosure generally relates to the production of polyethylene. More specifically, this disclosure relates to a process for hydrocarbon separation in a polyethylene production process.

BACKGROUND

In a typical polyethylene plant, a purge gas leaving a purge vessel upon purging a polyethylene polymer product may contain significant amounts of valuable hydrocarbons, including ethylene, isobutane, and comonomers. There are economic and environmental incentives to recover these hydrocarbons from the purge gas. Generally, a selective membrane based separation process or a pressure swing adsorption (PSA) process can be used for the recovery of hydrocarbons from the purge gas. The purge gas coming out of the purge vessel is usually sent through a compressor to increase the separation efficiency downstream of the compressor, whether the separation is done by selective membrane or by PSA. Recycle streams from the separation process can be sent back to the compressor; however, this increases the compressor load, which may limit the amount of purge gas that can be run through the separation process. Thus, there is an ongoing need for developing efficient processes for the recovery of hydrocarbons during polyethylene production.

BRIEF SUMMARY

Disclosed herein is a process for component separation in a polymer production system, comprising (a) separating a polymerization product stream into a gas stream and a polymer stream, wherein the polymer stream comprises polyethylene, isobutane, ethylene and ethane, (b) contacting at least a portion of the polymer stream with a purge gas in a purge vessel to yield a purged polymer stream and a spent purge gas stream, wherein the purged polymer stream comprises polyethylene, and wherein the spent purge gas stream comprises purge gas, isobutane, ethylene, and ethane, (c) introducing at least a portion of the spent purge gas stream to a compressor to produce a compressed gas stream, (d) introducing at least a portion of the compressed gas stream to a first separation unit to produce a first hydrocarbon stream and a membrane unit feed stream, wherein the first hydrocarbon stream comprises equal to or greater than about 50% of the isobutane of the compressed gas stream, and wherein the membrane unit feed stream comprises equal to or greater than about 95% of the purge gas of the compressed gas stream, (e) introducing at least a portion of the membrane unit feed stream to a membrane unit to produce a first recovered purge gas stream and a retentate stream, wherein the retentate stream comprises less than about 30% of the purge gas of the membrane unit feed stream, (f) introducing at least a portion of the retentate stream to a second separation unit to produce a second hydrocarbon stream and a pressure swing adsorption (PSA) unit feed stream, wherein the PSA unit feed stream comprises equal to or greater than about 97% of the purge gas of the retentate stream, and (g) introducing at least a portion of the PSA unit feed stream to a PSA unit to produce a second recovered purge gas stream and a tail gas stream, wherein a molar concentration of purge gas in the second recovered purge gas stream is greater than a molar concentration of purge gas in the first recovered purge gas stream.

Also disclosed herein is a process for component separation in a polymer production system, comprising (a) separating a polymerization product stream into a gas stream and a polymer stream, wherein the polymer stream comprises polyethylene, isobutane, ethylene and ethane, and wherein the gas stream comprises ethylene, ethane, and isobutene, (b) contacting at least a portion of the polymer stream with a nitrogen stream in a purge vessel to yield a purged polymer stream and a spent nitrogen stream, wherein the purged polymer stream comprises polyethylene, and wherein the spent nitrogen comprises nitrogen, isobutane, ethylene, and ethane, (c) introducing at least a portion of the spent nitrogen stream to a compressor to produce a compressed gas stream, (d) introducing at least a portion of the compressed gas stream to a first separation unit to produce a first hydrocarbon stream and a membrane unit feed stream, wherein the first hydrocarbon stream comprises equal to or greater than about 50% of the isobutane of the compressed gas stream, and wherein the membrane unit feed stream comprises equal to or greater than about 95% of the nitrogen of the compressed gas stream, (e) introducing at least a portion of the membrane unit feed stream to a nitrogen membrane unit to produce a first recovered nitrogen stream and a retentate stream, wherein the retentate stream comprises less than about 30% of the nitrogen of the membrane unit feed stream, (f) recycling a first portion of the first recovered nitrogen stream to the compressor and recycling a second portion of the first recovered nitrogen stream to the purge vessel, (g) introducing at least a portion of the retentate stream to a second separation unit to produce a second hydrocarbon stream and a pressure swing adsorption (PSA) unit feed stream, wherein the PSA unit feed stream comprises equal to or greater than about 97% of the nitrogen of the retentate stream, (h) introducing at least a portion of the PSA unit feed stream to a PSA unit to produce a second recovered nitrogen stream and a tail gas stream, wherein a molar concentration of nitrogen in the second recovered nitrogen stream is greater than a molar concentration of nitrogen in the first recovered nitrogen stream, and (i) recycling at least a portion of the tail gas stream to the compressor.

Further disclosed herein is a process for ethylene polymerization, comprising (a) polymerizing ethylene in a loop slurry reactor system to obtain a polymerization product stream, (b) separating at least a portion of the polymerization product stream in a flash chamber into a gas stream and a polymer stream comprising polyethylene, isobutane, ethylene and ethane, (c) contacting at least a portion of the polymer stream with nitrogen in a purge vessel to yield a purged polymer stream and a spent nitrogen stream, wherein the purged polymer stream comprises polyethylene, and wherein the spent nitrogen comprises nitrogen, isobutane, ethylene, and ethane, (d) introducing at least a portion of the spent nitrogen stream to a compressor to produce a compressed gas stream, (e) introducing at least a portion of the compressed gas stream to a first separation unit to produce a first hydrocarbon stream and a membrane unit feed stream, wherein the first hydrocarbon stream comprises equal to or greater than about 50% of the isobutane of the compressed gas stream, and wherein the membrane unit feed stream comprises equal to or greater than about 95% of the nitrogen of the compressed gas stream, (f) introducing at least a portion of the membrane unit feed stream to a nitrogen membrane unit to produce a first recovered nitrogen stream and a retentate stream, wherein the retentate stream comprises less than about 30% of the nitrogen of the membrane unit feed stream, (g) recycling a first portion of the first recovered nitrogen stream to the compressor, (h) recycling a second portion of the first recovered nitrogen stream to the purge vessel, (i) introducing at least a portion of the retentate stream to a second separation unit to produce a second hydrocarbon stream and a pressure swing adsorption (PSA) unit feed stream, wherein the PSA unit feed stream comprises equal to or greater than about 97% of the nitrogen of the retentate stream, (j) introducing at least a portion of the PSA unit feed stream to a PSA unit to produce a second recovered nitrogen stream and a tail gas stream, wherein a molar concentration of nitrogen in the second recovered nitrogen stream is greater than a molar concentration of nitrogen in the first recovered nitrogen stream, and (k) recycling at least a portion of the tail gas stream to the compressor.

BRIEF DESCRIPTION OF THE DRAWINGS

For a detailed description of the disclosed processes and systems, reference will now be made to the accompanying drawings in which.

DETAILED DESCRIPTION

Figure 1A:
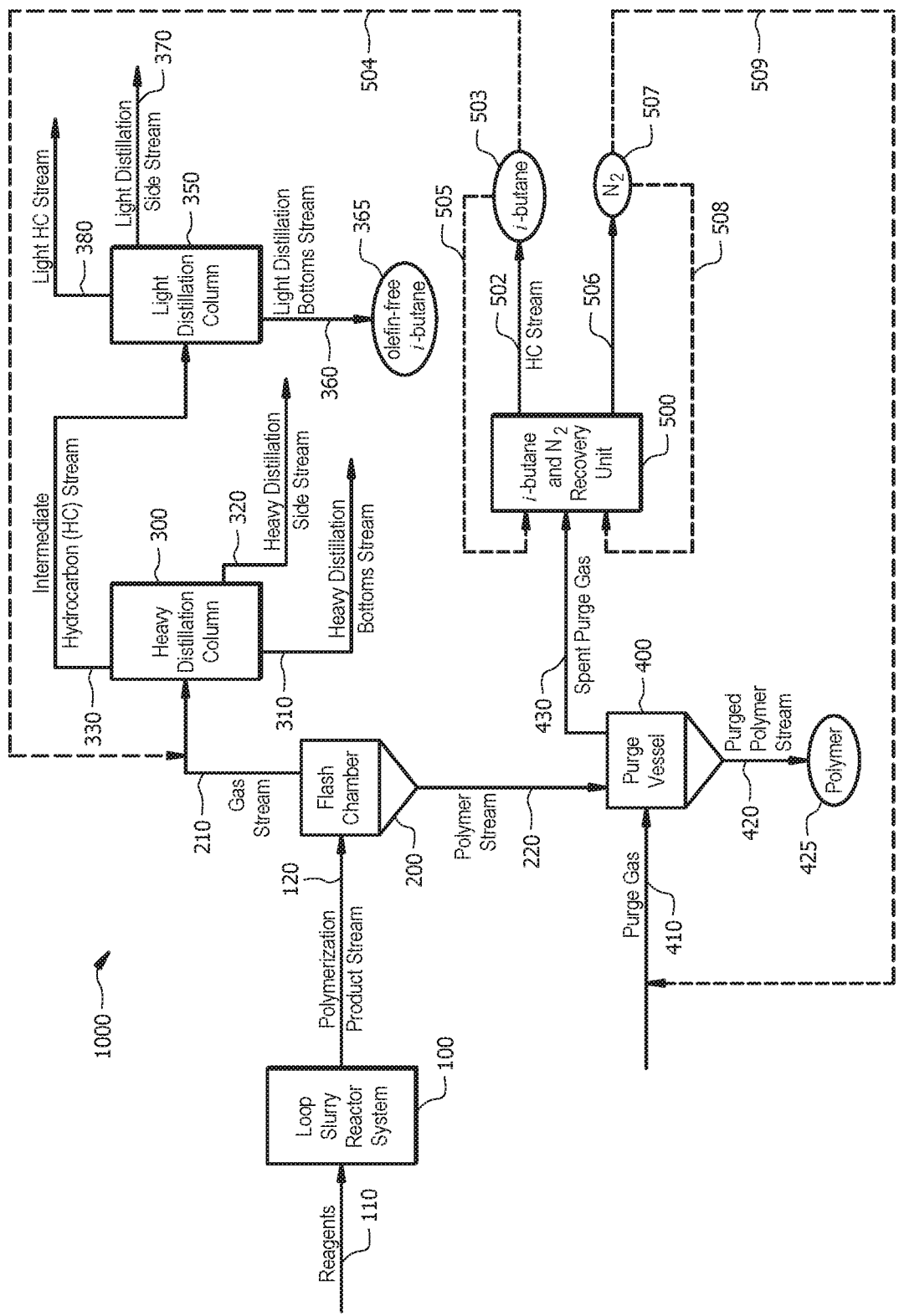
FIG. 1A illustrates a schematic of a polyethylene production system 1000.

It should be understood at the outset that although an illustrative implementation of one or more embodiments are provided below, the disclosed systems, methods, or both can be implemented using any number of techniques, whether currently known or in existence. The disclosure should in no way be limited to the illustrative implementations, drawings, and techniques illustrated below, including the exemplary designs and implementations illustrated and described herein, but can be modified within the scope of the appended claims along with their full scope of equivalents.

Disclosed herein are systems, apparatuses, and processes related to petrochemical production processes, for example the production of polyethylene. The systems, apparatuses, and processes are generally related to the separation of hydrocarbons (e.g., isobutane) from a composition resulting from petrochemical production processes, for example the production of polyethylene, and comprising the hydrocarbons and one or more other chemical components, compounds, or the like.

As disclosed herein, a process for component separation in a polymer production system (e.g., polyethylene production system) can generally comprise the steps of (a) separating a polymerization product stream into a gas stream and a polymer stream, wherein the polymer stream comprises polyethylene, isobutane, ethylene (e.g., unreacted ethylene), and ethane; (b) contacting at least a portion of the polymer stream with a purge gas (e.g., nitrogen) in a purge vessel to yield a purged polymer stream and a spent purge gas stream, wherein the purged polymer stream comprises polyethylene, and wherein the spent purge gas stream comprises purge gas, isobutane, ethylene, and ethane; (c) introducing at least a portion of the spent purge gas stream to a compressor to produce a compressed gas stream; (d) introducing at least a portion of the compressed gas stream to a first separation unit to produce a first hydrocarbon stream and a membrane unit feed stream, wherein the first hydrocarbon stream comprises equal to or greater than about 50% of the isobutane of the compressed gas stream, and wherein the membrane unit feed stream comprises equal to or greater than about 95% of the purge gas of the compressed gas stream; (e) introducing at least a portion of the membrane unit feed stream to a membrane unit to produce a first recovered purge gas stream and a retentate stream, wherein the retentate stream comprises less than about 30% of the purge gas of the membrane unit feed stream; (f) introducing at least a portion of the retentate stream to a second separation unit to produce a second hydrocarbon stream and a pressure swing adsorption (PSA) unit feed stream, wherein the PSA unit feed stream comprises equal to or greater than about 97% of the purge gas of the retentate stream; and (g) introducing at least a portion of the PSA unit feed stream to a PSA unit to produce a second recovered purge gas stream and a tail gas stream, wherein a molar concentration of purge gas in the second recovered purge gas stream is greater than a molar concentration of purge gas in the first recovered purge gas stream. The process can further comprise (i) recycling at least a portion of the first recovered purge gas stream to the compressor; and (ii) recycling at least a portion of the tail gas stream to the compressor; wherein the compressor has a volumetric flow that is reduced by at least about 20% when compared to a volumetric flow to a compressor in an otherwise similar polymer production system that has either a membrane unit or a PSA unit but not both.

As disclosed herein, a process for component separation in a polymer production system (e.g., polyethylene production system) can generally comprise selectively separating hydrocarbons (e.g., isobutane) from a spent purge gas (e.g., spent nitrogen used for purging a polymer product), wherein the spent purge gas can be recovered from a polymer production process. While the present disclosure will be discussed in detail in the context of a process for selectively separating hydrocarbons from a purge gas in a polyethylene production system, it should be understood that such process or any steps thereof can be applied in any suitable petrochemical production process requiring selective separation of hydrocarbons. The hydrocarbons can comprise any suitable hydrocarbons compatible with the disclosed methods and materials.

The following definitions are provided in order to aid those skilled in the art in understanding the detailed description of the present invention. Unless otherwise defined herein, scientific and technical terms used in connection with the present invention shall have the meanings that are commonly understood by those of ordinary skill in the art to which this invention belongs. Further, unless otherwise required by context, singular terms shall include pluralities and plural terms shall include the singular.

Unless explicitly stated otherwise in defined circumstances, all percentages, parts, ratios, and like amounts used herein are defined by weight.

Further, certain features of the present invention which are, for clarity, described herein in the context of separate embodiments, may also be provided in combination in a single embodiment. Conversely, various features of the invention that are, for brevity, described in the context of a single embodiment, may also be provided separately or in any sub-combination.

If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Regarding claim transitional terms or phrases, the transitional term "comprising," which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claim. A "consisting essentially of" claim occupies a middle ground between closed claims that are written in a "consisting of" format and fully open claims that are drafted in a "comprising" format. Absent an indication to the contrary, describing a compound or composition as "consisting essentially of" is not to be construed as "comprising," but is intended to describe the recited component that includes materials which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class to which it is utilized, and it is possible to have different transitional terms or phrases utilized with different features within a claim. For example, a method can comprise several recited steps (and other non-recited steps), but utilize a catalyst system consisting of specific components; alternatively, consisting essentially of specific components; or alternatively, comprising the specific components and other non-recited components.

In this disclosure, while systems, processes, and methods are often described in terms of "comprising" various components, devices, or steps, the systems, processes, and methods can also "consist essentially of" or "consist of" the various components, devices, or steps, unless stated otherwise.

The term "about" as used herein means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" may mean within 10% of the reported numerical value, preferably within 5% of the reported numerical value.

Although any methods, devices, and materials similar or equivalent to those described herein can be used in the practice or testing of the invention, the typical methods, devices, and materials are herein described.

Figure 1B:
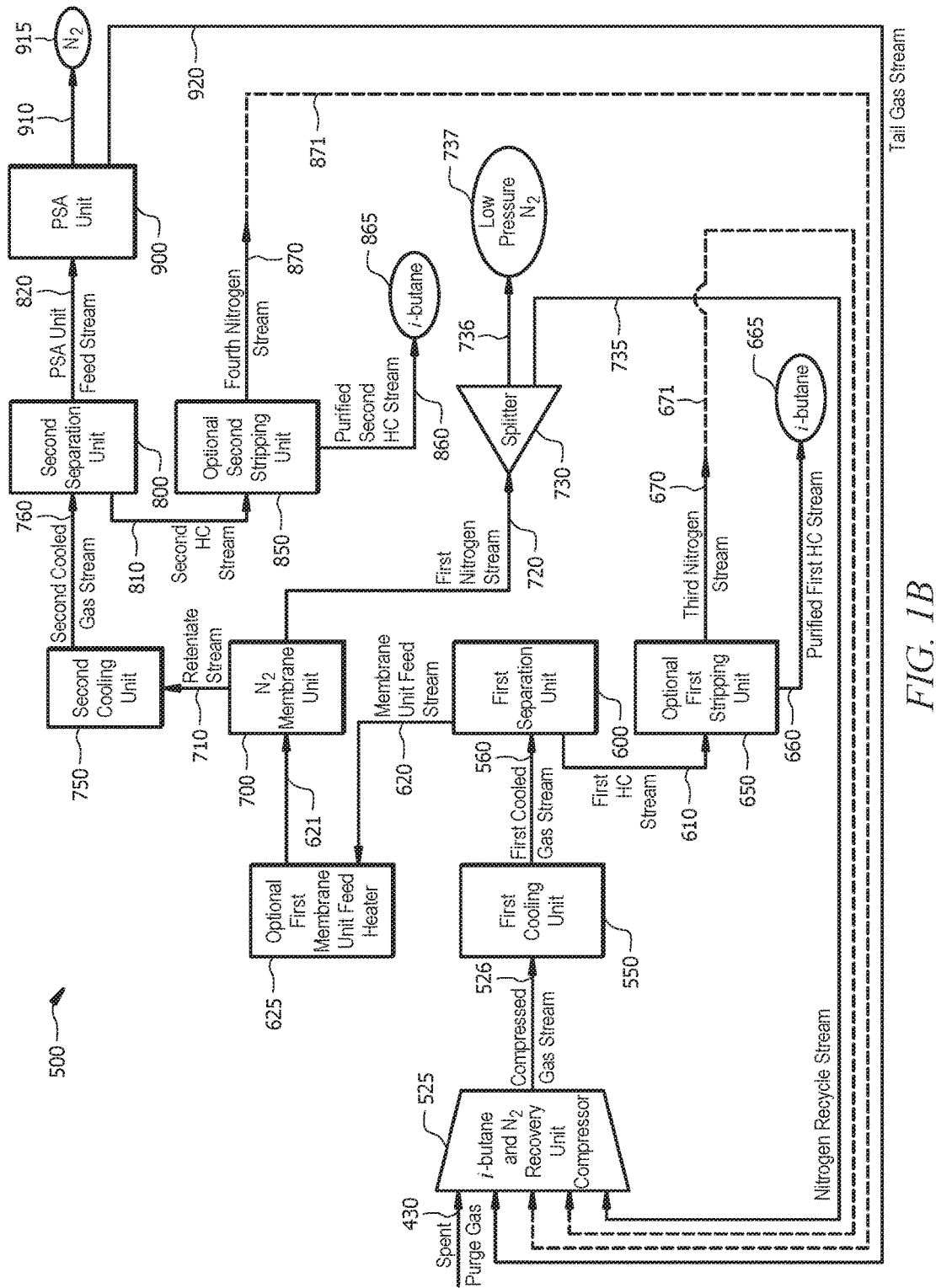
FIG. 1B illustrates a schematic of an isobutane and nitrogen recovery unit (INRU) 500.
Figure 1C:
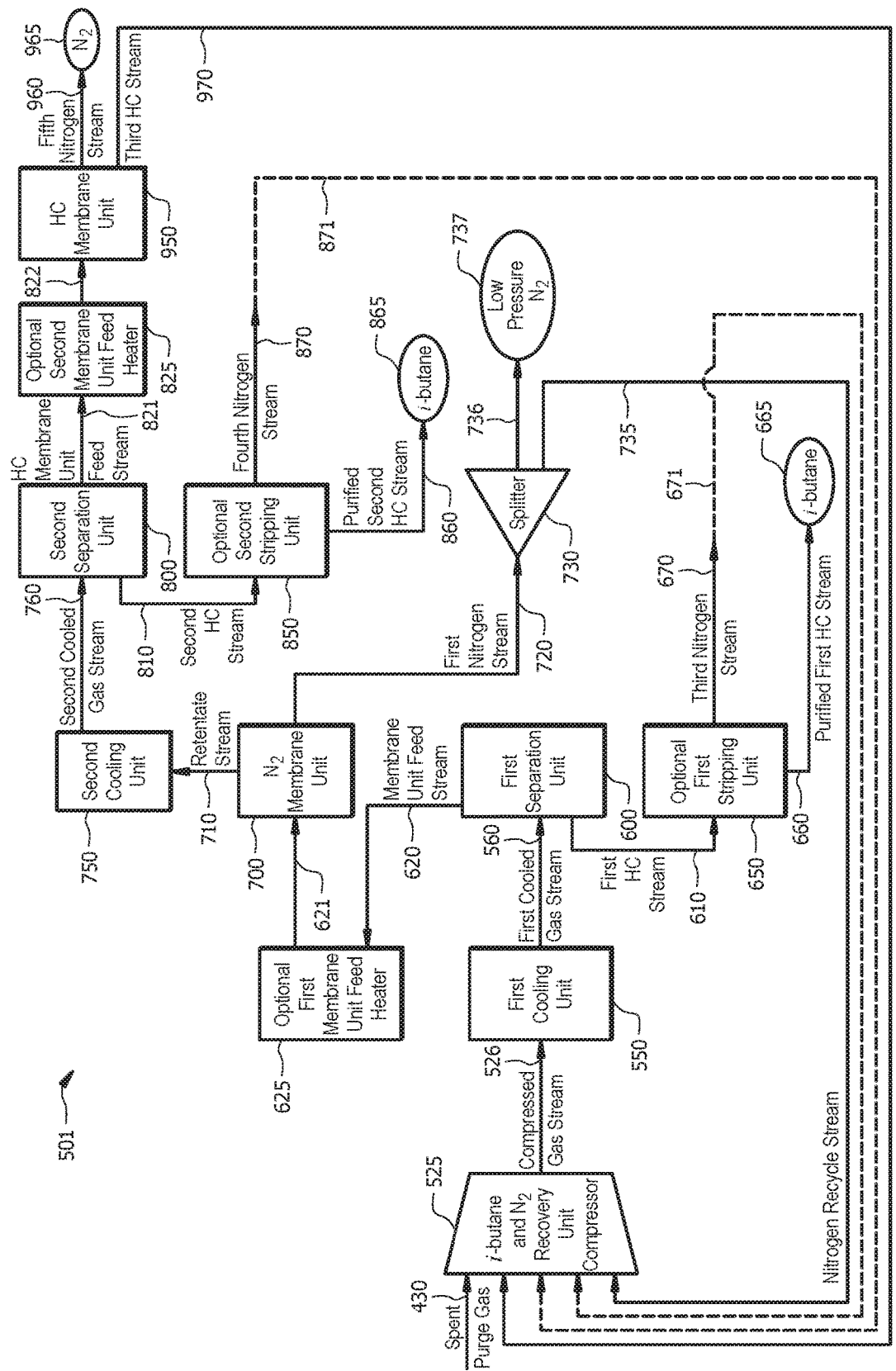
FIG. 1C illustrates a schematic of an INRU 501.

Referring to FIG. 1A, a polyethylene production (PEP) system 1000 is disclosed. PEP system 1000 generally comprises a loop slurry reactor system 100, a flash chamber 200, a heavy distillation column 300, a light distillation column 350, a purge vessel 400, and an isobutane (i-butane) and nitrogen recovery unit (INRU) 500 as shown in FIG. 1B, or alternatively INRU 501 as shown in FIG. 1C. In the PEP systems disclosed herein, various system components can be in fluid communication via one or more conduits (e.g., pipes, tubing, flow lines, etc.) suitable for the conveyance of a particular stream, for example as shown in detail by the numbered streams in FIG. 1A.

A reagents stream 110 (also referred to as a feed stream) can be communicated to the loop slurry reactor system 100. A polymerization product stream 120 can be communicated from the loop slurry reactor system 100 to the flash chamber 200. A gas stream 210 can be communicated from the flash chamber 200 to the heavy distillation column 300. The heavy distillation column 300 also can be referred to as a first distillation column. A heavy distillation bottoms stream 310, and a heavy distillation side stream 320 can be emitted from the heavy distillation column 300. An intermediate hydrocarbon (HC) stream 330 can be emitted from the heavy distillation column 300 and communicated to the light distillation column 350. The light distillation column 350 also can be referred to as a second distillation column. A light hydrocarbon stream 380, a light distillation side stream 370, and a light distillation bottoms stream 360 comprising olefin-free isobutane 365 can be emitted from the light distillation column 350. A polymer stream 220 can be communicated from the flash chamber 200 to the purge vessel 400. A purge gas stream 410 can be communicated to the purge vessel 400. A purged polymer stream 420 comprising a polymer 425 can be emitted from the purge vessel 400. A spent purge gas stream 430 can be communicated from the purge vessel 400 to the INRU 500. At least one hydrocarbon stream 502 comprising isobutane 503 and at least one nitrogen stream 506 comprising nitrogen 507 can be emitted from the INRU 500. At least a portion of the isobutane 503 can be recycled to one or more distillation columns. For example, at least a portion of the isobutane 503 can be recycled 504 to the heavy distillation column 300, for example via the gas stream 210. A portion of the isobutane 503 can be recycled 505 back to the INRU 500, for example to an INRU compressor. At least a portion of the nitrogen 507 can be recycled 509 to the purge vessel 400, for example via the purge gas stream 410. A portion of the nitrogen 507 can be recycled 508 back to the INRU 500, for example to an INRU compressor. The INRU 500 is shown in more detail in FIG. 1B, as will be described in more detail later herein. An alternative configuration of the INRU (e.g., INRU 501) is shown in more detail in FIG. 1C, as will be described in more detail later herein.

For purposes of the disclosure herein an "olefin-free" hydrocarbon (e.g., olefin-free isobutane) refers to a hydrocarbon (e.g., isobutane) that can be free of olefins, alternatively, substantially free of olefins, alternatively, essentially free of olefins, or alternatively, consist or consist essentially of non-olefins. Generally, olefins or alkenes are unsaturated hydrocarbons containing at least one carbon-carbon double bond. For example, olefins can be present in a substantially olefin-free hydrocarbon (e.g., substantially olefin-free isobutane) in an amount of less than about 10% by total weight of the olefin-free hydrocarbon, alternatively, less than about 9%, alternatively, less than about 8%, alternatively, less than about 7%, alternatively, less than about 6%, alternatively, less than about 5%, alternatively, less than about 4%, alternatively, less than about 3%, alternatively, less than about 2%, alternatively, less than about 1.0%, alternatively, less than about 0.5%, or alternatively, less than about 0.1%.

Referring to FIG. 1B, an INRU 500 is disclosed. INRU 500 generally comprises an INRU compressor 525, a first cooling unit 550, a first separation unit 600, an optional first membrane unit feed heater 625, an optional first stripping unit 650, a membrane unit 700, a splitter 730, a second cooling unit 750, a second separation unit 800, an optional second stripping unit 850, and a pressure swing adsorption (PSA) unit 900. In the INRU systems disclosed herein, various system components can be in fluid communication via one or more conduits (e.g., pipes, tubing, flow lines, etc.) suitable for the conveyance of a particular stream, for example as shown in detail by the numbered streams in FIG. 1B.

A spent purge gas stream 430 (e.g., same spent purge gas stream 430 entering INRU 500 in FIG. 1A) can be communicated from the purge vessel 400 to the INRU compressor 525. A compressed gas stream 526 can be communicated from the INRU compressor 525 to the first cooling unit 550. A first cooled gas stream 560 can be communicated from the first cooling unit 550 to the first separation unit 600. A first HC stream 610 can be recovered from the first separation unit 600 and can be optionally further processed in optional first stripping unit 650. A third recovered purge gas stream (e.g., third nitrogen stream) 670 can be emitted from the first stripping unit 650. At least a portion of the third recovered purge gas stream 670 can be recycled 671 to the INRU compressor 525 (e.g., via the recycle stream 508 as shown in FIG. 1A). A purified first HC stream 660 comprising isobutane 665 can be emitted from the first stripping unit 650. At least a portion of the isobutane 665 can be recycled to one or more distillation columns, for example via the recycle stream 504 as shown in FIG. 1A. For example, at least a portion of the isobutane 665 can be recycled to a heavy distillation column, such as the heavy distillation column 300, e.g., via the gas stream 210. A membrane unit feed stream 620 can be recovered from the first separation unit 600 and can be optionally communicated to the first membrane unit feed heater 625. A heated membrane unit feed stream 621 can be communicated from the first membrane unit feed heater 625 to the membrane unit (e.g., nitrogen membrane unit) 700. Alternatively, the membrane unit feed stream 620 can be communicated from the first separation unit 600 to the membrane unit (e.g., nitrogen membrane unit) 700 or otherwise flow unheated through stream 621. A first recovered purge gas stream (e.g., first nitrogen stream) 720 can be emitted from the membrane unit 700. At least a portion of the first recovered purge gas stream 720 can be communicated to the splitter 730. A first portion 735 of the first purge gas stream (e.g., nitrogen recycle stream) can be communicated from the splitter 730 to the INRU compressor 525 (e.g., via the recycle stream 508 as shown in FIG. 1A). A second portion 736 of the first purge gas stream comprising low pressure purge gas (e.g., low pressure nitrogen) 737 can be emitted from the splitter 730.

At least a portion of the low pressure purge gas 737 can be recycled to a purge vessel, such as the purge vessel 400, for example via the purge gas stream 410 (e.g., via the recycle stream 509 as shown in FIG. 1A). A retentate stream 710 can be communicated from the membrane unit 700 to the second cooling unit 750. A second cooled gas stream 760 can be communicated from the second cooling unit 750 to the second separation unit 800. A second HC stream 810 can be recovered from the second separation unit 800 and can be optionally further processed in optional second stripping unit 850. A fourth recovered purge gas stream (e.g., fourth nitrogen stream) 870 can be emitted from the second stripping unit 850. At least a portion of the fourth recovered purge gas stream 870 can be recycled 871 to the INRU compressor 525 (e.g., via the recycle stream 508 as shown in FIG. 1A). A purified second HC stream 860 comprising isobutane 865 can be emitted from the second stripping unit 850. At least a portion of the isobutane 865 can be recycled to one or more distillation columns, for example via the recycle stream 504 as shown in FIG. 1A. For example, at least a portion of the isobutane 865 can be recycled to a heavy distillation column, such as the heavy distillation column 300, for example via the gas stream 210. A PSA unit feed stream 820 can be communicated from the second separation unit 800 to the PSA unit 900. A second recovered purge gas stream (e.g., second nitrogen stream) 910 comprising nitrogen 915 can be emitted from the PSA unit 900. At least a portion of the nitrogen 915 can be recycled to a purge vessel, such as the purge vessel 400, for example via the purge gas stream 410 (e.g., via the recycle stream 509 as shown in FIG. 1A). A tail gas stream 920 can be communicated from the PSA unit 900 to the INRU compressor 525 (e.g., via the recycle stream 505 as shown in FIG. 1A).

Referring to FIG. 1C, an alternative configuration of an INRU (e.g., INRU 501) is disclosed. INRU 501 generally comprises an INRU compressor 525, a first cooling unit 550, a first separation unit 600, an optional first membrane unit feed heater 625, an optional first stripping unit 650, a membrane unit 700, a splitter 730, a second cooling unit 750, a second separation unit 800, an optional second stripping unit 850, an optional second membrane unit feed heater 825, and a hydrocarbon membrane unit 950. In the INRU systems disclosed herein, various system components can be in fluid communication via one or more conduits (e.g., pipes, tubing, flow lines, etc.) suitable for the conveyance of a particular stream, for example as shown in detail by the numbered streams in FIG. 1C. Unless otherwise indicated, the description of commonly enumerated components of INRU 500 of FIG. 1B applies to INRU 501 of FIG. 1C. Likewise, unless otherwise indicated, reference to INRU or INRU 500 includes the alternative configuration of INRU 501, and either INRU 500 or INRU 501 may be employed in the PEP system 1000 and the PEP process 2000.

Referring to FIG. 1C, a hydrocarbon membrane unit feed stream 821 can be recovered from the second separation unit 800 and can be optionally communicated to the second membrane unit feed heater 825. A heated hydrocarbon membrane unit feed stream 822 can be communicated from the second membrane unit feed heater 825 to the hydrocarbon membrane unit 950. Alternatively, the hydrocarbon membrane unit feed stream 821 can be communicated from the second separation unit 800 to the hydrocarbon membrane unit 950 or otherwise flow unheated through stream 822. A third hydrocarbon stream 970 comprising hydrocarbons (e.g., isobutane) can be emitted from the hydrocarbon membrane unit 950. At least a portion of the third hydrocarbon stream 970 can be communicated from the hydrocarbon membrane unit 950 to the INRU compressor 525 (e.g., via the recycle stream 505 as shown in FIG. 1A). A fifth recovered purge gas stream (e.g., fifth nitrogen stream) 960 comprising nitrogen 965 can be emitted from the hydrocarbon membrane unit 950. At least a portion of the nitrogen 965 can be recycled to a purge vessel, such as the purge vessel 400, for example via the purge gas stream 410 (e.g., via the recycle stream 509 as shown in FIG. 1A).

PEP system 1000 may be employed in the production of polyethylene according to one or more PEP processes as disclosed herein. Although the various steps of the PEP processes disclosed herein may be disclosed or illustrated in a particular order, such should not be construed as limiting the performance of these processes to any particular order unless otherwise indicated.

Figure 2:
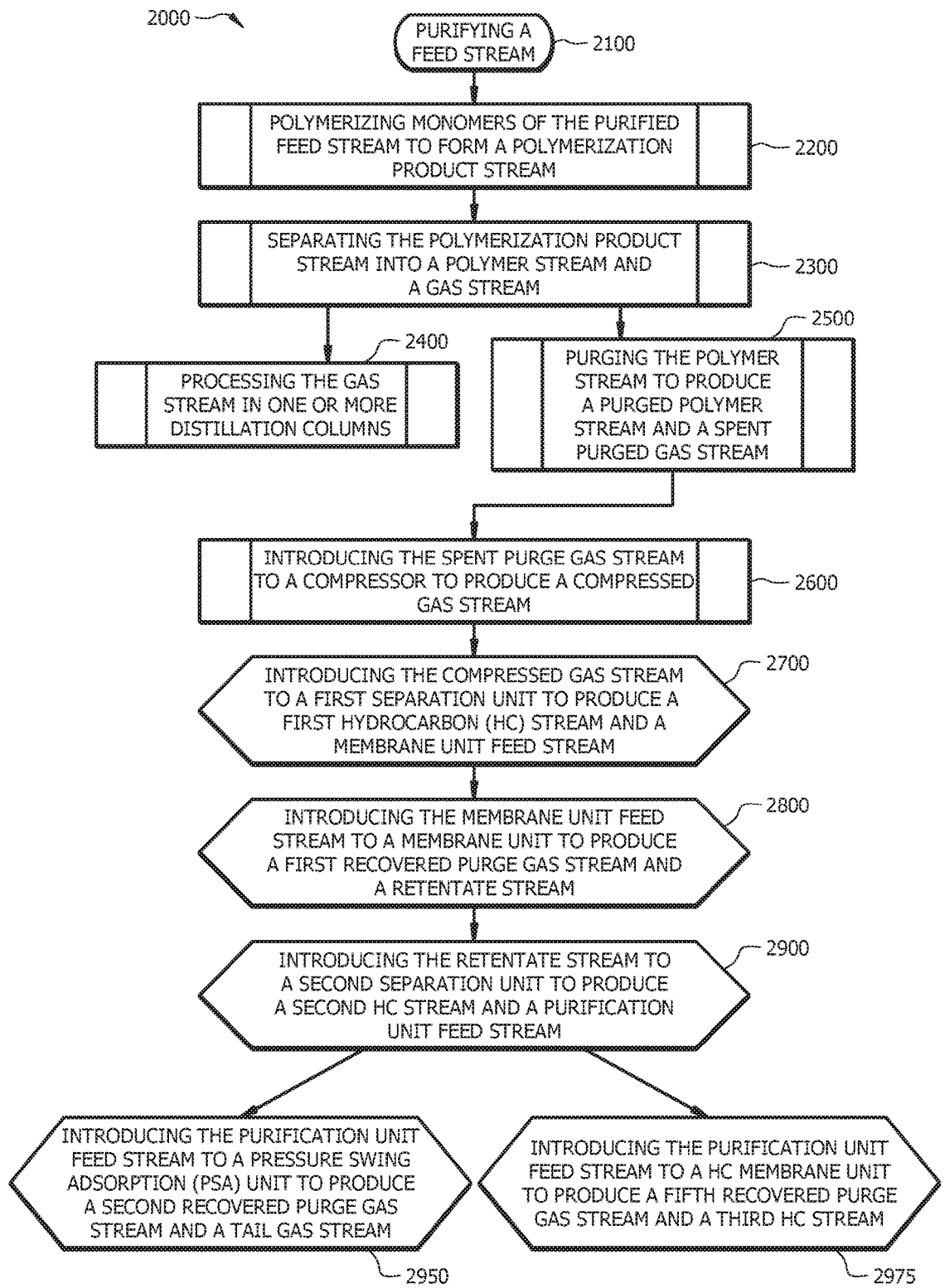
FIG. 2 illustrates a flow diagram of a polyethylene production process.

Referring to FIG. 2, a PEP process 2000 is illustrated. PEP process 2000 can generally comprise (i) an optional step 2100 of purifying a feed stream; (ii) a step 2200 of polymerizing monomers of the purified feed stream to form a polymerization product stream; (iii) a step 2300 of separating the polymerization product stream into a polymer stream and a gas stream; (iv) a step 2400 of processing the gas stream in a gas treatment system (e.g., comprising one or more distillation columns); (v) a step 2500 of purging the polymer stream to produce a purged polymer stream and a spent purge gas stream; (vi) a step 2600 of introducing the spent purge gas stream to a compressor to produce a compressed gas stream; (vii) a step 2700 of introducing the compressed gas stream to a first separation unit to produce a first HC stream and a membrane unit feed stream; (viii) a step 2800 of introducing the membrane unit feed stream to a membrane unit to produce a first recovered purge gas stream and a retentate stream; (ix) a step 2900 of introducing the retentate stream to a second separation unit to produce a second HC stream and a purification unit feed stream; and (x) a step 2950 of introducing the purification unit feed stream (e.g., PSA unit feed stream) to a PSA unit to produce a second recovered purge gas stream and a tail gas stream, or (xi) a step 2975 of introducing the purification unit feed stream (e.g., HC membrane unit feed stream) to a HC membrane unit to produce a third HC stream and a fifth recovered purge gas stream. The PEP process 2000 or a portion thereof can be implemented via the PEP system 1000 (e.g., as illustrated in FIG. 1A). For examples, steps 2600 through 2950 or 2975 can be implemented via the INRU systems 500 or 501, respectively.

The PEP process 2000 can generally comprise the step 2100 of purifying a feed stream or a reagents stream. Purifying a feed stream can comprise separating unwanted compounds and elements from a feed stream comprising ethylene to form a purified feed stream. Purifying a feed stream can comprise any suitable method or process, including the nonlimiting examples of filtering, membrane screening, reacting with various chemicals, absorbing, adsorbing, distillation(s), or combinations thereof.

Figure 3:
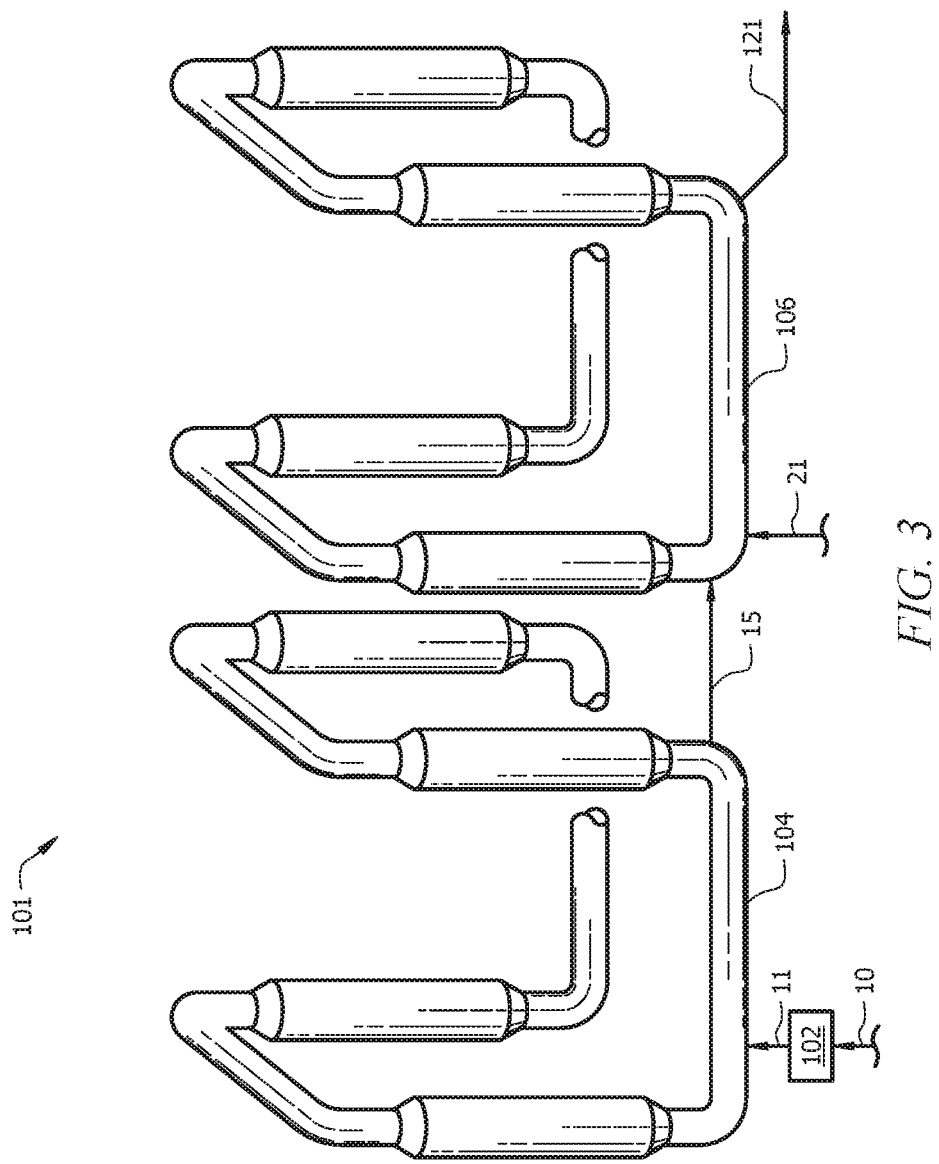
FIG. 3 illustrates a schematic of a loop slurry reactor system.

Referring to FIG. 3, a loop slurry reactor system 101 is shown, wherein a feed stream 10 (e.g., reagents stream 110 in FIG. 1A) can be communicated to a purifier 102. The feed stream 10 can comprise ethylene and various other gases, such as but not limited to methane, ethane, acetylene, propane, propylene, water, nitrogen, oxygen, various other gaseous hydrocarbons having three or more carbon atoms, various contaminants, or combinations thereof. The purifier 102 can comprise a device or apparatus suitable for the purification of one or more reactant gases in a feed stream comprising a plurality of potentially unwanted gaseous compounds, elements, contaminants, and the like. Nonlimiting examples of a suitable purifier 102 can comprise a filter, a membrane, a reactor, an absorbent, a molecular sieve, one or more distillation columns, or combinations thereof. The purifier 102 can be configured to separate ethylene from a stream comprising a plurality of potentially unwanted gaseous compounds, elements, contaminants, and the like.

Purifying a feed stream can yield a purified feed stream 11 comprising substantially pure monomers (e.g., substantially pure ethylene). The purified feed stream can comprise less than about 25% by total weight of the stream, alternatively, less than about 10%, alternatively, less than about 1.0% of any one or more of nitrogen, oxygen, methane, ethane, propane, comonomers, or combinations thereof. As used herein "substantially pure ethylene" refers to a fluid stream comprising at least about 60% ethylene, alternatively, at least about 70% ethylene, alternatively, at least about 80% ethylene, alternatively, at least about 90% ethylene, alternatively, at least about 95% ethylene, alternatively, at least about 99% ethylene by total weight of the stream, or alternatively, at least about 99.5% ethylene by total weight of the stream. The feed stream 11 can further comprise trace amounts of ethane.

The purified feed stream can comprise a comonomer, such as unsaturated hydrocarbons having from 3 to 20 carbon atoms. Nonlimiting examples of comonomers that can be present in the purified feed stream include alpha olefins, such as for example propylene, 1-butene, 1-pentene, 1-hexene, 3-methyl-1-butene, 4-methyl-1-pentene, 1-heptene, 1-octene, 1-nonene, 1-decene, and the like, or combinations thereof.

The PEP process 2000 can generally comprise the step 2200 of polymerizing monomers of the purified feed stream to form a polymerization product stream. The polymerization product stream can be formed using any suitable olefin polymerization method which can be carried out using various types of polymerization reactors.

As used herein, the terms "polymerization reactor" or "reactor" include any polymerization reactor capable of polymerizing olefin monomers or comonomers to produce homopolymers or copolymers. Such homopolymers and copolymers are referred to as resins or polymers. The various types of reactors include those that can be referred to as gas phase, batch, slurry, solution, high-pressure, tubular or autoclave reactors. Gas phase reactors can comprise fluidized bed reactors or staged horizontal reactors. Slurry reactors can comprise vertical or horizontal loops. High-pressure reactors can comprise autoclave or tubular reactors. Reactor types can include batch or continuous processes. Continuous processes could use intermittent or continuous product discharge. Processes can also include partial or full direct recycle of unreacted monomer, unreacted comonomer, diluent, or combinations thereof.

Polymerization reactor systems of the present disclosure can comprise one type of reactor in a system or multiple reactors of the same or different type. Production of polymers in multiple reactors can include several stages in at least two separate polymerization reactors interconnected by transfer stream(s), line(s), apparatus(es) (for example, a separation vessel(s)), device(s) (for example, a valve or other mechanism), or combinations thereof, making it possible to transfer the polymers resulting from a first polymerization reactor into a second reactor. The desired polymerization conditions in one of the reactors can be different from the operating conditions of the other reactors. Alternatively, polymerization in multiple reactors can include the manual transfer of polymer from one reactor to subsequent reactors for continued polymerization. Multiple reactor systems can include any combination including, but not limited to, multiple loop reactors. Multiple reactor systems can include any combination including, but not limited to, multiple loop reactors, multiple gas phase reactors, or a combination of loop and gas phase reactors. The multiple reactors can be operated in series, in parallel, or both.

According to one aspect of this disclosure, the polymerization reactor system can comprise at least one loop slurry reactor comprising vertical or horizontal loops. Monomer, diluent, catalyst, and optionally any comonomer can be continuously fed to a loop reactor where polymerization occurs. Generally, continuous processes can comprise the continuous introduction of a monomer, an optional comonomer, a catalyst, and a diluent into a polymerization reactor and the continuous removal from this reactor of a suspension comprising polymer particles and the diluent. Reactor effluent can be flashed to remove the solid polymer from the liquids that comprise the diluent, monomer, comonomer, or combinations thereof. Various technologies can be used for this separation step including but not limited to, flashing that can include any combination of heat addition and pressure reduction; separation by cyclonic action in either a cyclone or hydrocyclone; or separation by centrifugation.

A suitable slurry polymerization process (also known as the particle form process), is disclosed, for example, in U.S. Pat. Nos. 3,248,179; 4,501,885; 5,565,175; 5,575,979; 6,239,235; 6,262,191; and 6,833,415; each of which is incorporated by reference herein in its entirety.

Suitable diluents used in slurry polymerization include, but are not limited to, the monomer, and optionally, the comonomer, being polymerized and hydrocarbons that are liquids under reaction conditions. Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used.

According to another aspect of this disclosure, the polymerization reactor can comprise at least one gas phase reactor. Such polymerization reactors can employ a continuous recycle stream containing one or more monomers continuously cycled through a fluidized bed in the presence of a catalyst under polymerization conditions. A recycle stream can be withdrawn from the fluidized bed and recycled back into the reactor. Simultaneously, a polymer product can be withdrawn from the reactor and new or fresh monomer can be added to replace the polymerized monomer. Likewise, copolymer product can optionally be withdrawn from the reactor and new or fresh comonomer can be added to replace polymerized comonomer, polymerized monomer, or combinations thereof. In some configurations, gas phase reactors can employ a diluent, such as isopentane. Such gas phase reactors can comprise a process for multi-step gas phase polymerization of olefins, in which olefins are polymerized in the gaseous phase in at least two independent gas phase polymerization zones while feeding a catalyst-containing polymer formed in a first polymerization zone to a second polymerization zone. Gas phase reactors are disclosed in U.S. Pat. Nos. 5,352,749; 4,588,790; and 5,436,304; each of which is incorporated by reference herein in its entirety.

According to yet another aspect of this disclosure, a high-pressure polymerization reactor can comprise a tubular reactor or an autoclave reactor. Tubular reactors, autoclave reactors, or both can have several zones where fresh monomer (optionally, comonomer), or a polymerization catalyst system can be added. Monomer (optionally, comonomer) can be entrained in an inert dense fluid stream (well above the critical point at such high pressures) and introduced into the reactor (typically introduced in multiple locations on the reactor). Polymerization catalyst system components can be entrained in a monomer feed stream, introduced as liquids or supercritical fluids directly into the reactor, or both. The fluid streams can be intermixed in the reactor to initiate and sustain polymerization. Heat and pressure can be employed appropriately to obtain optimal polymerization reaction conditions.

According to still yet another aspect of this disclosure, the polymerization reactor can comprise a solution polymerization reactor wherein the monomer (optionally, comonomer) can be contacted with a catalyst composition by suitable stirring or other means. A carrier comprising an inert organic diluent or excess monomer (optionally, comonomer) can be employed. If desired, the monomer and/or optional comonomer can be brought in the vapor phase into contact with a catalytic reaction product, in the presence or absence of liquid material. A polymerization zone is maintained at temperatures and pressures that will result in the formation of a solution of the polymer in a reaction medium. Agitation can be employed to obtain better temperature control and to maintain uniform polymerization mixtures throughout the polymerization zone. Adequate means are utilized for dissipating the exothermic heat of polymerization.

Polymerization reactors suitable for the disclosed systems and processes can further comprise any combination of at least one raw material feed system, at least one feed system for catalyst or catalyst components, and at least one polymer recovery system. Suitable reactor systems can further comprise systems for feedstock purification, catalyst storage and preparation, extrusion, reactor cooling, polymer recovery, fractionation, recycle, storage, loadout, laboratory analysis, and process control.

Conditions (e.g., polymerization conditions) that are controlled for polymerization efficiency and to provide desired resin properties include temperature; pressure; type of catalyst or co-catalyst, quantity of catalyst or co-catalyst, or both; concentrations of various reactants; partial pressures of various reactants; or combinations thereof.

Polymerization temperature can affect catalyst productivity, polymer molecular weight and molecular weight distribution. Suitable polymerization temperature can be any temperature below the de-polymerization temperature according to the Gibbs Free energy equation. The polymerization temperature can have as upper limit a temperature at which the monomer (e.g., ethylene) begins to decompose. As will be appreciated by one of skill in the art, and with the help of this disclosure, monomer decomposition temperatures are pressure dependent. Polymerization temperatures can be from about 60° C. to about 350° C., alternatively from about 60° C. to about 280° C., or alternatively from about 70° C. to about 110° C., depending upon the type of polymerization reactor.

Suitable pressures will also vary according to the reactor and polymerization type. The pressure for liquid phase polymerizations in a loop reactor is typically less than about 1,000 pound per square inch gauge (psig) (6.9 megapascal (MPa)). Pressure for gas phase polymerization is usually at about 200 psig (1.4 MPa) to about 700 psig (4.8 MPa). High-pressure polymerization in tubular or autoclave reactors is generally run at about 10,000 psig (68.9 MPa) to about 50,000 psig (344.7 MPa). Polymerization reactors can also be operated in a supercritical region occurring at generally higher temperatures and pressures. Operation above the critical point of a pressure/temperature diagram (supercritical phase) can offer advantages. In an aspect, polymerization can occur in an environment having a suitable combination of temperature and pressure. For example, polymerization can occur at a pressure in a range of from about 550 psig (3.8 MPa) to about 650 psig (4.5 MPa), or alternatively, from about 600 psig (4.1 MPa) to about 625 psig (4.3 MPa) and a temperature in a range of from about 170° F. (77° C.) to about 230° F. (110° C.), or alternatively, from about 195° F. (91° C.) to about 220° F. (104° C.).

The concentration of various reactants can be controlled to produce resins with certain physical and mechanical properties. The proposed end-use product that will be formed by the resin and the method of forming that product determines the desired resin properties. Mechanical properties include tensile, flexural, impact, creep, stress relaxation and hardness tests. Physical properties include density, molecular weight, molecular weight distribution, melting temperature, glass transition temperature, temperature melt of crystallization, density, stereoregularity, crack growth, long chain branching and rheological parameters.

The concentrations, partial pressures, or both of monomer, comonomer, hydrogen, co-catalyst, modifiers, and electron donors are important in producing these resin properties. Comonomer can be used to control product density. Hydrogen can be used to control product molecular weight. Cocatalysts can be used to alkylate, scavenge poisons and control molecular weight. Modifiers can be used to control product properties and electron donors affect stereoregularity, the molecular weight distribution, molecular weight, or combinations thereof. In addition, the concentration of poisons is minimized because poisons impact the reactions and product properties.

Any suitable polymerization catalyst system can be employed. A suitable polymerization catalyst system can comprise a catalyst and, optionally, a co-catalyst (e.g., organoaluminum compound), a promoter, or both. In some aspects, the catalyst system can comprise an activator (e.g., activator-support). Nonlimiting examples of suitable catalyst systems include but are not limited to single-site or dual-site catalysts such as Ziegler Natta catalysts, Ziegler catalysts, chromium catalysts, chromium oxide catalysts, chrome-silica catalysts, chrome-titania catalysts, chromocene catalysts, metallocene catalysts, nickel catalysts, or combinations thereof. Suitable metallocene catalysts for use in the systems described herein may be any conventional or non-conventional metallocene catalyst. As used herein, the term "metallocene" is used to refer to all catalytically active metals: η-ligand complexes in which a metal is complexed by one, two, or more open chain or closed-ring η-ligands. The use of bridged bis-η-ligand metallocenes, single η-ligand "half metallocenes", and bridged η-σ ligand "scorpionate" metallocenes is preferred in accordance with some aspects of the present disclosure. The metal in such complexes is preferably a group 4A, 5A, 6A, 7A or 8A metal or a lanthanide or actinide of the Periodic Table of the Elements, especially a group 4A, 5A or 6A metal, more particularly Zr, Hf or Ti. The η-ligand preferably comprises $\eta^4$ or $\eta^5$ open-chain or a $\eta^5$-cyclopentadienyl ring, optionally with a ring or chain carbon replaced by a heteroatom (e.g., N, B, S or P), optionally substituted by pendant or fused ring substituents and optionally linked by bridge (e.g., a 1 to 4 atom bridge such as $(CH_2)_2$, $C(CH_3)_2$ or $Si(CH_3)_2$) to a further optionally substituted homo or heterocyclic cyclopentadienyl ring. The ring substituents may for example be halo atoms or alkyl groups optionally with carbons replaced by heteroatoms such as O, N and Si, especially Si and O and optionally substituted by mono or polycyclic groups such as phenyl or naphthyl groups. Catalyst systems suitable for use in the present disclosure have been described, for example, in U.S. Pat. Nos. 7,163,906; 7,619,047; 7,790,820; 7,960,487; 8,138,113; 8,207,280; 8,268,944; 8,450,436; and 9,181,372; each of which is incorporated by reference herein in its entirety.

In an aspect of the present disclosure, the catalyst system can comprise an activator. The activator can be a solid oxide activator-support, a chemically treated solid oxide, a clay mineral, a pillared clay, an exfoliated clay, an exfoliated clay gelled into another oxide matrix, a layered silicate mineral, a non-layered silicate mineral, a layered aluminosilicate mineral, a non-layered aluminosilicate mineral, an aluminoxane, a supported aluminoxane, an ionizing ionic compound, an organoboron compound, or any combination thereof. The terms "chemically-treated solid oxide," "solid oxide activator-support," "acidic activator-support," "activator-support," "treated solid oxide compound," and the like are used herein to indicate a solid, inorganic oxide of relatively high porosity, which exhibits Lewis acidic or Brønsted acidic behavior, and which has been treated with an electron-withdrawing component, typically an anion, and which is calcined. The electron-withdrawing component is typically an electron-withdrawing anion source compound. Thus, the chemically-treated solid oxide compound comprises the calcined contact product of at least one solid oxide compound with at least one electron-withdrawing anion source compound. Typically, the chemically-treated solid oxide comprises at least one ionizing, acidic solid oxide compound. The terms "support" and "activator-support" are not used to imply these components are inert, and such components should not be construed as an inert component of the catalyst composition.

Monomers in a feed stream (e.g., purified feed stream 11) can be polymerized in the presence of the catalyst system. Polymerizing monomers of the purified feed stream can comprise allowing a polymerization reaction between a plurality of monomers by contacting a monomer or monomers with a catalyst system under conditions suitable for the formation of a polymer. Polymerizing comonomers of the purified feed stream can comprise allowing a polymerization reaction between a plurality of comonomers by contacting a comonomer or comonomers with a catalyst system under conditions suitable for the formation of a copolymer.

In an aspect of this disclosure, the step 2200 of polymerizing monomers of the purified feed stream to form a polymerization product stream can be carried out using a loop slurry reactor system (e.g., loop slurry reactor system 100 in FIG. 1), such as for example a loop slurry reactor system 101 illustrated in FIG. 3. The loop slurry reactor system 101 generally comprises a purifier 102, a first reactor 104, and an optional second reactor 106. In the loop slurry reactor system disclosed herein, various system components can be in fluid communication via one or more conduits (e.g., pipes, tubing, flow lines, etc.) suitable for the conveyance of a particular stream, for example as shown in detail by the numbered streams in FIG. 3.

A purified feed stream 11 can be communicated from the purifier 102 to one or more of the reactors (e.g., a first reactor 104, a second reactor 106). Where the loop slurry reactor system comprises two or more reactors, a mid-polymerization reactor stream 15 can be communicated from the first reactor 104 to the second reactor 106. Hydrogen can be introduced to the first reactor 104, the second reactor 106, or both. Hydrogen can be introduced into the second reactor 106 in stream 21. A polymerization product stream (e.g., polymerization product stream 121 in FIG. 3, polymerization product stream 120 in FIG. 1) can be emitted from the first reactor 104, the second reactor 106, or both.

As illustrated by FIG. 3, polymerizing monomers of the purified feed stream can comprise routing the purified feed stream 11 to the one or more of the polymerization reactors 104, 106. Polymerizing monomers of the mid-polymerization reactor stream 15 can comprise routing the mid-polymerization reactor stream 15 to polymerization reactor(s) 106. As illustrated by FIG. 3, polymerizing monomers of the mid-polymerization reactor stream 15 can comprise routing the mid-polymerization reactor stream 15 from polymerization reactor(s) 104 to polymerization reactor(s) 106.

The polymerization reactors 104, 106 can comprise any vessel or combination of vessels suitably configured to provide an environment for a chemical reaction (e.g., a contact zone) between monomers (e.g., ethylene), polymers (e.g., an "active" or growing polymer chain), or both, and optionally comonomers, copolymers, or both in the presence of a catalyst to yield a polymer (e.g., a polyethylene polymer), copolymer, or both. Although FIG. 3 illustrate a PEP system having two reactors in series, one of skill in the art viewing this disclosure will recognize that one reactor, alternatively, any suitable number of reactors, configuration of reactors, or both can be employed.

As illustrated in FIG. 3, production of polymers in multiple reactors can include at least two polymerization reactors 104, 106 interconnected by one or more devices or apparatus (e.g., valve, continuous take-off valve, continuous take-off mechanism). As illustrated in FIG. 3, production of polymers in multiple reactors can include at least two polymerization reactors 104, 106 interconnected by one or more streams or lines (e.g., mid-polymerization reactor stream 15). Production of polymers in multiple reactors can include at least two polymerization reactors 104, 106 interconnected by one or more separators (e.g., flash chambers).

Polymerizing monomers can comprise introducing a suitable catalyst system into the first reactor 104, the second reactor 106, or both, respectively, so as to form a slurry. Alternatively, a suitable catalyst system can reside in the first reactor 104, the second reactor 106, or both, respectively.

As previously described herein, polymerizing monomers can comprise selectively manipulating one or more polymerization reaction conditions to yield a given polymer product, to yield a polymer product having one or more desirable properties, to achieve a desired efficiency, to achieve a desired yield, and the like, or combinations thereof. Polymerizing monomers of the purified feed stream 11 can comprise adjusting one or more polymerization reaction conditions.

Polymerizing monomers can comprise maintaining a suitable temperature, pressure, partial pressure(s), or combinations thereof during the polymerization reaction; alternatively, cycling between a series of suitable temperatures, pressures, partial pressure(s), or combinations thereof during the polymerization reaction.

Polymerizing monomers can comprise polymerizing comonomers in one or more of polymerization reactors 104, 106. Polymerizing monomers can comprise introducing ethylene monomer, a comonomer, or both to the polymerization reactor 106.

Polymerizing monomers can include introducing hydrogen into one or more of reactors 104 and 106. For example, FIG. 3 illustrates that hydrogen can be introduced into reactor 106 through stream 21. The amount of hydrogen introduced into the reactor 106 can be adjusted so as to obtain, in the diluent, a molar ratio of hydrogen to ethylene of 0.001 to 0.1. This molar ratio can be at least 0.004 in reactor 106, and in some instances this molar ratio cannot exceed 0.05. The ratio of the concentration of hydrogen in the diluent in reactor 104 to the concentration of hydrogen polymerization reactor 106 can be at least 20, alternatively, at least 30, alternatively, at least 40, alternatively, not greater than 300, or alternatively, not greater than 200. Suitable hydrogen concentration control methods and systems are disclosed in U.S. Pat. No. 6,225,421, which is incorporated by reference herein in its entirety.

Polymerizing monomers can comprise circulating, flowing, cycling, mixing, agitating, or combinations thereof, the monomers (optionally, comonomers), catalyst system, the slurry within the reactors 104, 106, the slurry between the reactors 104, 106, or combinations thereof. Where the monomers (optionally, comonomers), catalyst system, slurry, or combinations thereof are circulated, circulation can be at a velocity (e.g., slurry velocity) of from about 1 m/s to about 30 m/s, alternatively, from about 2 m/s to about 17 m/s, or alternatively, from about 3 m/s to about 15 m/s.

Polymerizing monomers can comprise configuring reactors 104, 106 to yield an unimodal resin. Herein, the "modality" of a polymer resin refers to the form of its molecular weight distribution curve, i.e., the appearance of the graph of the polymer weight fraction as a function of its molecular weight. The polymer weight fraction refers to the weight fraction of molecules of a given size. A polymer having a molecular weight distribution curve showing a single peak can be referred to as a unimodal polymer, a polymer having a curve showing two distinct peaks can be referred to as bimodal polymer, a polymer having a curve showing three distinct peaks can be referred to as trimodal polymer, etc.

Polymerizing monomers can comprise configuring reactors 104, 106 to yield a multimodal (e.g., a bimodal) polymer (e.g., polyethylene). For example, the resultant polymer can comprise both a relatively high molecular weight, low density (HMWLD) polyethylene polymer and a relatively low molecular weight, high density (LMWHD) polyethylene polymer. For example, various types of suitable polymers can be characterized as having a various densities. For example, a Type I polymer can be characterized as having a density in a range of from about 0.910 g/cm$^3$ to about 0.925 g/cm$^3$, alternatively, a Type II polymer can be characterized as having a density from about 0.926 g/cm$^3$ to about 0.940 g/cm$^3$, alternatively, a Type III polymer can be characterized as having a density from about 0.941 g/cm$^3$ to about 0.959 g/cm$^3$, alternatively, a Type IV polymer can be characterized as having a density of greater than about 0.960 g/cm$^3$.

As illustrated in FIG. 3, polymerizing monomers of the purified feed stream 11 can yield the polymerization product stream 121. The polymerization product stream 121 (e.g., polymerization product stream 120 in FIG. 1) can generally comprise various solids, semi-solids, volatile and nonvolatile liquids, gases and combinations thereof. Polymerizing monomers of the purified feed stream 11 can yield the polymerization product stream 121 generally comprising unreacted monomer (e.g., ethylene), optional unreacted comonomer, by-products (e.g., ethane, which can be by-product ethane formed from ethylene and hydrogen), and a polymerization product (e.g., polymer and optionally, copolymer). As used herein, an "unreacted monomer," for example, ethylene, refers to a monomer that was introduced into a polymerization reactor during a polymerization reaction but was not incorporated into a polymer. As used herein, an "unreacted comonomer" refers to a comonomer that was introduced into a polymerization reactor during a polymerization reaction but was not incorporated into a polymer. The solids, liquids, or both of the polymerization product stream 121 can comprise a polymer product (e.g., a polyethylene polymer), often referred to at this stage of the PEP process as "polymer fluff." The gases of the polymerization product stream 121 can comprise unreacted, gaseous reactant monomers or optional comonomers (e.g., unreacted ethylene monomers, unreacted comonomers), gaseous waste products, gaseous contaminants, or combinations thereof.

The polymerization product stream 121 can comprise hydrogen, nitrogen, methane, ethylene, ethane, propylene, propane, butane, 1-butene, isobutane, pentane, hexane, 1-hexene and heavier hydrocarbons. Ethylene can be present in a range of from about 0.1% to about 15%, alternatively, from about 1.5% to about 5%, or alternatively, from about 2% to about 4% by total weight of the polymerization product stream. Ethane can be present in a range of from about 0.001% to about 4%, or alternatively, from about 0.2% to about 0.5% by total weight of the polymerization product stream. Isobutane can be present in a range of from about 80% to about 98%, alternatively, from about 92% to about 96%, or alternatively, about 95% by total weight of the polymerization product stream.

The PEP process 2000 can generally comprise the step 2300 of separating the polymerization product stream into a polymer stream and a gas stream. Separating the polymerization product into a polymer stream and a gas stream can generally comprise removing gases from liquids, solids (e.g., the polymer fluff), or both by any suitable process.

As illustrated by FIG. 1, separating the polymerization product into a polymer stream and a gas stream can comprise routing the polymerization product stream 120 to a separator (e.g., flash chamber 200). The polymerization product stream 120 can comprise at least a portion of the polymerization product stream 121 emitted from the second reactor 106. The polymerization product stream 120 can comprise at least a portion of the mid-polymerization reactor stream 15 emitted from the first reactor 104. The polymerization product stream 120 can comprise at least a portion of the polymerization product stream 121 and at least a portion of the mid-polymerization reactor stream 15.

A separator such as flash chamber 200 can be configured to separate a stream (e.g., polymerization product stream 120 comprising polyethylene) into gases, liquids, solids, or combinations thereof.

The separator for separating the polymerization product stream into a polymer stream and a gas stream can comprise a vapor-liquid separator. As will be appreciated by one of skill in the art, and with the help of this disclosure, the solids of the polymerization product stream (e.g., polymer fluff) are slurried in the liquids of the polymerization product stream, and a vapor-liquid separator would generally separate the solids and the liquid in a single slurry phase from the gases of the polymerization product stream. Nonlimiting examples of separators suitable for use in the present disclosure include a fixed-bed adsorption column, a flash tank, a filter, a membrane, a reactor, an absorbent, an adsorbent, a molecular sieve, or combinations thereof.

The separator may be a flash tank (e.g., flash chamber 200). Without wishing to be limited by theory, such a flash tank can comprise a vessel configured to vaporize, remove, or both low vapor pressure components from a high temperature fluid, a high pressure fluid, or a high temperature and a high pressure fluid. The separator for separating the polymerization product into a polymer stream and a gas stream can be configured such that an incoming stream can be separated into a liquid stream (e.g., a condensate stream) and a gas (e.g., vapor) stream. The liquid stream can comprise a reaction product (e.g., polyethylene, often referred to as "polymer fluff"). The liquid stream can be a bottoms stream. The gas or vapor stream can comprise volatile solvents, gaseous, unreacted monomers, unreacted optional comonomers, waste gases (secondary reaction products, such as contaminants and the like), or combinations thereof. The gas stream can be an overhead stream.

The separator for separating the polymerization product into a polymer stream and a gas stream can be configured such that the polymerization product stream is flashed by heat, pressure reduction, or both, such that an enthalpy of the polymerization product stream is increased. This can be accomplished via a heater, a flashline heater, various other operations commonly known in the art, or combinations thereof. For example, a flash line heater comprising a double pipe can exchange heat by hot water or steam. Such a flashline heater can increase the temperature of the stream while reducing its pressure.

Separating the polymerization product stream into a polymer stream and a gas stream can comprise distilling, vaporizing, flashing, filtering, membrane screening, centrifuging, absorbing, adsorbing, or combinations thereof, the polymerization product. As illustrated in FIG. 1, separating the polymerization product stream into a polymer stream and a gas stream yields a gas stream 210 and a polymer stream 220 (e.g., polyethylene polymer, copolymer).

The gas stream 210 can comprise unreacted monomer (e.g., unreacted ethylene monomer), optional unreacted comonomer, and various gases. Gas stream 210 can comprise the non-solid components of polymerization product stream 120 in a vapor phase. The gas stream 210 can comprise hydrogen, nitrogen, methane, ethylene, ethane, propylene, propane, butane, isobutane, pentane, hexane, 1-hexene, heavier hydrocarbons, or combinations thereof. The gas stream 210 can further comprise trace amounts of oxygen. Ethylene can be present in a range of from about 0.1% to about 15%, alternatively, from about 1.5% to about 5%, or alternatively, about 2% to about 4% by total weight of the gas stream. Ethane can be present in a range of from about 0.001% to about 4%, or alternatively, from about 0.2% to about 0.5% by total weight of the gas stream. Isobutane can be present in a range from about 80% to about 98%, alternatively, from about 92% to about 96%, or alternatively, about 95% by total weight of the gas stream.

The mid-polymerization reactor stream 15 can be processed in a similar manner to the polymerization product stream 121, wherein the mid-polymerization reactor stream 15 can be separated into a mid-polymerization polymer stream and a mid-polymerization gas stream. The mid-polymerization polymer stream can be communicated to the second reactor 106; processed in a similar manner to the polymer stream 220, as will be described in more detail later herein; communicated to the purge vessel 400, such as for example via the polymer stream 220; or combinations thereof. The mid-polymerization gas stream can be processed in a similar manner to the gas stream 210, as will be described in more detail later herein; can be communicated to the heavy distillation column 300, such as for example via the gas stream 210; or both.

The PEP process 2000 can generally comprise the step 2400 of processing the gas stream in one or more distillation columns. Processing the gas stream 210 can comprise separating at least one gaseous component from the gas stream. While the step of processing the gas stream will be discussed in detail in the context of two distillation columns used for such processing of the gas stream, it should be understood that any suitable number of distillation columns can be used for processing the gas stream, such as for example one, two, three, four, five, or more distillation columns.

Separating at least one gaseous component from the gas stream can comprise distilling a gas stream (e.g., gas stream 210) in one step so as to allow at least one gaseous component to separate from other gaseous components according to temperature(s) of boiling. Separating at least one gaseous component from the gas stream can comprise distilling a gas stream into a light hydrocarbon stream comprising ethylene, ethane, optionally hydrogen, or combinations thereof. Separating at least one gaseous component from the gas stream can comprise collecting hexane, hexene, optionally isobutane, or combinations thereof in a distillation bottoms stream.

Alternatively, separating at least one gaseous component from the gas stream can comprise collecting isobutane from a side stream of a distillation column, a distillation bottoms stream of a distillation column, or both.

As shown in FIG. 1, distillation columns 300 and 350 can be configured to separate at least one gaseous component from a gas stream (e.g., gas stream 210). Processing the gas stream 210 in one or more distillation columns can yield several hydrocarbon fractions. The gas stream 210 can be communicated to the heavy distillation column 300. Gas stream 210 can be distilled in the heavy distillation column 300 to form an intermediate hydrocarbon (HC) stream 330 which can be communicated to the light distillation column 350. Non-distilled components in the heavy distillation column 300 can emit from the heavy distillation column 300 in heavy distillation bottoms stream 310. Heavy distillation side stream 320 can optionally emit from the heavy distillation column 300.

Intermediate hydrocarbon stream 330 can be characterized as comprising, alternatively, comprising substantially, alternatively, consisting essentially of, alternatively, consisting of, $C_4$ and lighter hydrocarbons (e.g., butane, isobutane, propane, ethane, or methane) and any light gases (e.g., nitrogen). For example, $C_4$ and lighter hydrocarbons and gases can be present in the intermediate hydrocarbon stream 330 in an amount of from about 80% to about 100% by total weight of the intermediate hydrocarbon stream, alternatively from about 90% to about 99.999999%, alternatively from about 99% to about 99.9999%, alternatively, $C_5$ and heavier hydrocarbons can be present in the intermediate hydrocarbon stream 330 in an amount from about 0% to about 20% by total weight of the intermediate hydrocarbon stream, alternatively from about 10% to about 0.000001%, alternatively from about 1.0% to about 0.0001%. Also, for example, at least 90% by weight of the $C_4$ and lighter hydrocarbons and gases of the gas stream 210 can be present in the intermediate hydrocarbon stream 330, alternatively, at least 98%, alternatively, at least 99%.

Heavy distillation bottoms stream 310 can be characterized as comprising $C_6$ and heavy components, wherein the heavy components can comprise alkanes, that is, alkanes larger than hexane (e.g., heptane, other large alkanes, or both). Hydrocarbons other than $C_6$ and heavy alkanes can be present in the heavy distillation bottoms stream 310 in an amount less than about 15%, alternatively, less than about 10%, alternatively, less than about 5% by total weight of the heavy distillation bottoms stream 310. In an aspect, the heavy distillation bottoms stream 310 can be directed to additional processing steps or methods, or alternatively they can be disposed of, as appropriate. In an aspect, heavy distillation bottoms stream 310 can be incinerated.

Heavy distillation side stream 320 can be characterized as comprising hexene. For example, hexene can be present in heavy distillation side stream 320 in an amount of from about 20% to about 98% by total weight of the heavy distillation side stream 320, alternatively from about 40% to about 95%, or alternatively from about 50% to about 95%.

The heavy distillation side stream 320 can be recycled. Recycling the heavy distillation side stream 320 can comprise routing (e.g., via a suitable pump or compressor) the heavy distillation side stream 320 back to one or more components of the PEP system 1000, introducing the heavy distillation side stream 320 into one or more components of the PEP system 1000, or both; for example, into loop slurry reactor system 100 for reuse in a polymerization reaction. Recycling the heavy distillation side stream 320 can provide efficient means, cost-effective means, or both of supplying hexene for operation of the polymerization reaction process. At least a portion of the hexene of the heavy distillation side stream 320 can be employed in the polymerization reaction as, for example, a comonomer in the reaction. Alternatively, at least a portion of the heavy distillation side stream 320 can be routed to storage for subsequent use in a polymerization reaction or employed in any other suitable process. As will be appreciated by one of skill in the art, and with the help of this disclosure, at least a portion of the hexene can be recycled back to the reactor when the reactor is undergoing a polymerization reaction involving hexene as a comonomer. Further, as will be appreciated by one of skill in the art, and with the help of this disclosure, at least a portion of the hexene can be stored when the reactor is undergoing a polymerization reaction in the absence of hexene.

At least a portion of the heavy distillation bottoms stream 310, heavy distillation side stream 320, or both can be returned to the heavy distillation column 300. For example, at least a portion of the heavy distillation bottoms stream 310, heavy distillation side stream 320, or both can be routed via a reboiler to the heavy distillation column 300 for additional processing.

Heavy distillation column 300 can be provided with one or more inlets and at least two outlets. The heavy distillation column 300 can be operated at a suitable temperature and pressure, for example as can be suitable to achieve separation of the components of the gas stream 210. For example, the heavy distillation column 300 can be operated at a temperature in a range of from about 15° C. to about 233° C., alternatively, from about 20° C. to about 200° C., alternatively, from about 20° C. to about 180° C.; a pressure in a range of from about 14.7 pound per square inch (psi) to about 527.9 psi, alternatively, from about 15.7 psi to about 348 psi, alternatively, from about 85 psi to about 290 psi; or both. The heavy distillation column 300 can be configured, sized, or both to provide for separation of a suitable volume of gases (e.g., a flash gas stream). As will be appreciated by one of skill in the art viewing this disclosure, the gas stream 210 can remain, reside, or both within heavy distillation column 300 for any suitable amount of time, for example an amount of time as can be necessary to provide sufficient separation of the components within the heavy distillation column 300.

The gas stream 210 can be introduced into the heavy distillation column 300 without a compressive step, that is, without compression of the gas stream 210 after it is emitted from the flash chamber 200 and before it is introduced into the heavy distillation column 300. Alternatively, the gas stream 210 can be introduced into the heavy distillation column 300 at substantially the same pressure as the outlet pressure of flash chamber 200 (e.g., a pressure of from about 14.7 pound per square inch absolute (psia) to about 527.9 psia, alternatively, from about 15.7 psia to about 348 psia, alternatively, from about 85 psia to about 290 psia at the outlet of the flash chamber 200). Alternatively, the gas stream 210 can be introduced into the heavy distillation column 300 without a significant compressive step. Gas stream 210 can be introduced into heavy distillation column 300 at a pressure in a range of from about 25 psi less than the pressure at which the gas stream 210 was emitted from the flash chamber 200 to about 25 psi greater than the pressure at which the gas stream 210 was emitted from the flash chamber 200, alternatively, from about 15 psi less than the pressure at which the gas stream 210 was emitted from the flash chamber 200 to about 15 psi greater than the pressure at which the gas stream 210 was emitted from the flash chamber 200, alternatively, from about 5 psi less than the pressure at which the gas stream 210 was emitted from the flash chamber 200 to about 5 psi greater than the pressure at which the gas stream 210 was emitted from the flash chamber 200. The gas stream 210 can be introduced into the heavy distillation column 300 at a pressure in a range of from about 14.7 psia to about 527.8 psia, alternatively, from about 15.7 psia to about 348 psia, or alternatively, from about 85 psia to about 290 psia.

The heavy distillation column 300 can be configured, operated, or both such that each of the intermediate hydrocarbon stream 330, the heavy distillation bottoms stream 310, and an optionally the heavy distillation side stream 320 can comprise a desired portion, part, or subset of components of the gas stream 210. For example, as will be appreciated by one of skill in the art and with the help of this disclosure, the location of a particular stream outlet, the operating parameters of the heavy distillation column 300, the composition of the gas stream 210, or combinations thereof can be manipulated such that a given stream can comprise a particular one or more components of the gas stream 210.

As shown in FIG. 1, the intermediate hydrocarbon stream 330 can be separated in the light distillation column 350 to form light hydrocarbon stream 380, light distillation bottoms stream 360, and optionally, light distillation side stream 370. At least one gaseous component can be emitted from the light distillation column 350 in the light hydrocarbon stream 380, and the other gaseous components can be emitted from the light distillation column 350 in the light distillation bottoms stream 360.

Light hydrocarbon stream 380 can be characterized as comprising ethylene. For example, ethylene can be present in light hydrocarbon stream 380 in an amount from about 50% to about 99% by total weight of the light hydrocarbon stream 380, alternatively from about 60% to about 98%, or alternatively, from about 70% to about 95%.

The light hydrocarbon stream 380 can further comprise other light gases (e.g., ethane, methane, carbon dioxide, nitrogen, hydrogen, or combinations thereof). In some aspects, the light hydrocarbon stream 380 can comprise ethylene and ethane.

Light distillation bottoms stream 360 can be characterized as comprising propane, butane, isobutane, pentane, hexane, heavier saturated hydrocarbons, or combinations thereof. The light distillation bottoms stream 360 can be free of olefins, alternatively, substantially free of olefins, alternatively, essentially free of olefins, alternatively, consisting essentially of or consisting of non-olefins. For example, olefins can be present in the light distillation bottoms stream 360 in an amount of less than about 1.0% by total weight of the light distillation bottoms stream 360, alternatively, less than about 0.5%, alternatively, less than about 0.1%. The light distillation bottoms stream 360 can comprise olefin-free isobutane 365.

Light distillation side stream 370 can be characterized as comprising isobutane. Light distillation side stream 370 comprising, alternatively, consisting of or essentially consisting of, isobutane can be emitted from the light distillation column 350. The isobutane of the light distillation bottoms stream 360 can comprise a different grade of isobutane than the isobutane of the light distillation side stream 370. For example, the light distillation bottoms stream 360 can comprise isobutane that is substantially free of olefins, and the light distillation side stream 370 can comprise a recycle isobutane which can include olefins.

At least a portion of the light distillation side stream 370, the light distillation bottoms stream 360, or both can be recycled. Recycling at least a portion of the light distillation side stream 370, light distillation bottoms stream 360, or both can comprise routing (e.g., via a suitable pump or compressor) or introducing at least a portion of the light distillation side stream 370, the light distillation bottoms stream 360, or both back to one or more components of the PEP system 1000, for example, into loop slurry reactor system 100 for reuse in a polymerization reaction. At least a portion of the light distillation side stream 370, the light distillation bottoms stream 360, or both can be combined with various other components (catalysts, cocatalysts, etc.) to form a catalyst slurry that can be introduced into one or more of reactors 104, 106. Without wishing to be limited by theory, because at least a portion of light distillation bottoms stream 360 can be free of olefins and can comprise isobutane, the light distillation bottoms stream 360 can be mixed with catalytic components (e.g., catalysts, cocatalysts, etc.) without the risk of unintended polymerization reactions (e.g., polymerization prior to introduction into the one or more reactors). As such, at least a portion of the light distillation bottoms stream 360 can serve as a source of olefin-free isobutane for a polymerization reaction. Recycling at least a portion of the light distillation side stream 370, the light distillation bottoms stream 360, or both can provide efficient means, cost-effective means, or both of supplying isobutane for operation of the polymerization reaction process. Additionally or alternatively, at least a portion of the light distillation side stream 370, the light distillation bottoms stream 360, or both can be routed to storage for subsequent use in a polymerization reaction or employed in any other suitable process.

At least a portion of the light distillation side stream 370, the light distillation bottoms stream 360, or both can be returned to the light distillation column 350. For example, at least a portion of the light distillation side stream 370, the light distillation bottoms stream 360, or both can be routed via a reboiler to the light distillation column 350 for additional processing.

The light distillation column 350 can be configured, sized, or both to provide for separation of a suitable volume of gases. For example, the light distillation column 350 can be operated at a temperature in a range of from about 50° C. to about 20° C., alternatively, from about 40° C. to about 10° C., alternatively, from about 30° C. to about 5° C.; and a pressure in a range of from about 14.7 psia to about 529.7 psia, alternatively, from about 15.7 psia to about 348 psia, alternatively, from about 85 psia to about 290 psia. The light distillation column 350 can be configured, sized, or both to provide for separation of a suitable volume of intermediate hydrocarbon stream 330. As will be appreciated by one of skill in the art, and with the help of this disclosure, the intermediate hydrocarbon stream 330 can remain, reside, or both within the light distillation column 350 for any suitable amount of time as can be necessary to provide sufficient separation of the components of the intermediate hydrocarbon stream 330. The light distillation column 350 can be provided with at least two outlets.

The light distillation column 350 can be configured, operated, or both such that each of the light hydrocarbon stream 380 and the light distillation bottoms stream 360 can comprise a desired portion, part, or subset of components of the intermediate hydrocarbon stream 330. For example, as will be appreciated by one of skill in the art with the aid of this disclosure, the location of a particular stream inlet or outlet, the operating parameters of the light distillation column 350, the composition of the intermediate hydrocarbon stream 330, or combinations thereof can be manipulated such that a given stream can comprise a particular one or more components of the intermediate hydrocarbon stream 330.

The PEP process 2000 can generally comprise the step 2500 of purging the polymer stream to produce a purged polymer stream and a spent purge gas stream. As shown in FIG. 1, a primary solids feed to the purge vessel 400 comprises typically the polymer stream 220. Generally, the polymer stream 220 comprises a solids discharge (e.g., polyolefin fluff, such as for example polyethylene fluff) that exits the flash chamber 200. A purpose of the purge vessel 400 is to remove residual hydrocarbon from polymer stream 220 and to provide a substantially-clean polymer fluff (e.g., polymer 425) with relatively small amounts of entrained volatile organic content. The polymer 425 (e.g., polymer fluff) can be transported or conveyed to an extrusion/loadout system for conversion to pellets, for distribution and sale as polyolefin pellet resin, or both.

Referring to FIG. 1, the polymer stream 220 can comprise a polymer (e.g., polyethylene), unreacted monomer (e.g., ethylene, 1-hexene) and various gases (e.g., ethane, isobutane, hydrogen, methane, propane, butane, pentane, hexane, propylene). Processing (e.g., purging) the polymer stream 220 can yield the purged polymer stream 420 and the spent purge gas stream 430 generally comprising a purge gas (e.g., nitrogen), unreacted monomer (e.g., ethylene, 1-hexene), and various gases (e.g., ethane, isobutane, hydrogen, nitrogen, methane, propylene, propane, butane, pentane, hexane, heavier hydrocarbons).

Referring to FIG. 1, a purge gas 410 (e.g., an inert gas, nitrogen) can be circulated through purge vessel 400 to remove residual hydrocarbons via a spent purge gas stream 430. The spent purge gas stream 430 can be communicated to a compressor, such as for example an INRU compressor 525, for hydrocarbon recovery.

The purge vessel 400 can be a cylindrical vessel having a relatively tall vertical section, a cover or head at the top, sloped sides or conical shape at the bottom with an opening for polymer fluff discharge. The polymer fluff to be degassed of volatile hydrocarbons can enter the vessel at the top, while the purge gas, typically nitrogen, can be introduced to the vessel in the sloped bottom sides. Flow can be countercurrent between the purge gas and polymer fluff in the vessel. In certain aspects, a hydrocarbon rich purge gas (e.g., spent purge gas 430) can leave the purge vessel through an opening at the top, while a degassed fluff (e.g., purged polymer stream 420) can leave at the bottom of the purge vessel. Purge gas can be introduced to the purge vessel 400 at various vessel heights (as opposed to just at the bottom of the vessel), wherein the purge gas might be characterized by relatively low purity, but it would still help remove a portion of entrained gases from the polymer fluff. For example, a low purity nitrogen stream, such as nitrogen stream 736, could be introduced to the purge vessel 400 at a point higher than the bottom of the purge vessel (e.g., about mid-way through the height of the vessel), to aid in degassing the polymer fluff.

Degassing effectiveness in the purge vessel can be predicated on the maintenance of an uniform plug flow of the polymer fluff and purge gas in the purge vessel, thereby ensuring good contact between the two. A diameter (D) of the purge vessel can typically range from about 5 to about 6 feet, but a length (L) of the purge vessel can be chosen to achieve a residence time (e.g., from about 30 to about 180 minutes) sufficient for degassing the polymer fluff. L/D ratios can range from about 4 to about 8; however, L/D ratios can be outside this range. Internal features can be employed in the purge vessel, such as a distributor plate for introducing purge gas (e.g., nitrogen), an inverted cone for facilitating plug flow of the polymer (e.g., to reduce bridging or channeling of the polymer fluff), and the like.

Processing the purged polymer stream 420 (e.g., polymer 425) comprises any suitable process or series of processes configured to produce a polymer product as can be suitable for commercial or industrial usage, storage, transportation, further processing, or combinations thereof.

Processing the purged polymer stream 420 can comprise routing the purged polymer stream 420 to a polymer processor. The polymer processor can be configured for the performance of a suitable processing means (e.g., to form various articles), nonlimiting examples of which include cooling, injection molding, melting, pelletizing, film blowing, cast film, blow molding, extrusion molding, rotational molding, thermoforming, cast molding, fiber spinning, and the like, or combinations thereof. Various additives and modifiers can be added to the polymer to provide better processing during manufacturing and for desired properties in the end product. Nonlimiting examples of such additives can include surface modifiers such as slip agents, antiblocks, tackifiers; antioxidants such as primary and secondary antioxidants; pigments; processing aids such as waxes/oils and fluoroelastomers; special additives such as fire retardants, antistats, scavengers, absorbers, odor enhancers, and degradation agents; or combinations thereof.

The polymer can include other suitable additives. Such additives can be used singularly or in combination and can be included in the polymer before, during or after preparation of the polymer as described herein. Such additives can be added via known techniques, for example during an extrusion or compounding step such as during pelletization or subsequent processing into an end use article.

The polymer processor can be configured to form a suitable polymer product. Nonlimiting examples of suitable polymer products as can result from processing the purged polymer stream include films, powders, pellets, resins, liquids, or any other suitable form as will be appreciated by those of skill in the art. Such a suitable output can be for use in, for example, one or more of various consumer or industrial products. For example, the polymer product can be utilized in any one or more of various articles, including, but not limited to, bottles, drums, toys, containers, household containers, utensils, film products, tanks, fuel tanks, pipes, membranes, geomembranes, and liners. The polymer processor can be configured to form pellets for transportation to a consumer product manufacturer.

The PEP process 2000 can generally comprise introducing the spent purge gas stream to an INRU, such as INRU 500 or 501, to produce hydrocarbons (e.g., isobutane, such as isobutane 503) and purge gas (e.g., nitrogen, such as nitrogen 507). In an aspect, at least one gaseous component (e.g., hydrocarbons, isobutane; purge gas, nitrogen) can be separated from the spent purge gas stream 430 during step 2600.

As disclosed herein, separating at least one gaseous component from a gas stream (e.g., the spent purge gas stream 430) generally comprises any suitable method of selectively separating at least a first chemical component or compound from a stream comprising the first chemical component or compound and one or more other chemical components, compounds, or the like.

The gaseous component separated from the gas stream can comprise one or more hydrocarbons. Nonlimiting examples of such hydrocarbons include alkanes (e.g., ethane, butane, isobutane, hexane, and the like, or combinations thereof). The gaseous component separated from the gas stream can comprise isobutane. Capturing isobutane can result in a savings of the cost of the captured isobutane and reduce the presence of isobutane in flare emissions. The gaseous component separated from the gas stream can comprise a purge gas such as nitrogen. Capturing nitrogen can result in a savings of the cost of the captured nitrogen that can be recycled to various units in the PEP system 1000, INRU system 500, or both. Nonlimiting examples of suitable separating means include distilling, vaporizing, flashing, filtering, membrane screening, absorbing, adsorbing, molecular weight exclusion, size exclusion, polarity-based separation, or combinations thereof.

The PEP process 2000 can generally comprise the step 2600 of introducing the spent purge gas stream to a compressor, such as INRU compressor 525, to produce a compressed gas stream. The INRU compressor 525 can comprise any suitable gas compressor that can increase the pressure of the spent purge gas stream 430 as required by the PEP process 2000. Generally, a gas compressor is a mechanical device that can increase the pressure of a gas by reducing its volume. Nonlimiting examples of INRU compressors suitable for use in the present disclosure include a gas compressor, a screw compressor, a rotary-screw compressor, an oil-free rotary-screw compressor, and oil-injected rotary-screw compressor, a centrifugal compressor, a reciprocating compressor, an axial-flow compressor, and the like, or combinations thereof.

The spent purge gas stream 430 can be characterized by a pressure (e.g., inlet pressure, compressor inlet pressure) of from about 14.7 psia (0.101 MPa) to about 100 psia (0.689 MPa), alternatively from about 16 psia (0.110 MPa) to about 30 psia (0.207 MPa), or alternatively from about 17 psia (0.117 MPa) to about 25 psia (0.172 MPa). The compressed gas stream 526 emitted from the INRU compressor 525 can be characterized by a pressure (e.g., outlet pressure, compressor outlet pressure) of from about 150 psi (1.03 MPa) to about 500 psi (3.45 MPa), alternatively from about 200 psi (1.38 MPa) to about 400 psi (2.76 MPa), or alternatively from about 225 psi (1.55 MPa) to about 300 psi (2.07 MPa). As will be appreciated by one of skill in the art, and with the help of this disclosure, the composition of the spent purge gas stream is not affected by compressing it, and as such the composition of the compressed gas stream is the same as the composition of the spent purge gas stream. Further, as will be appreciated by one of skill in the art, and with the help of this disclosure, compressing the spent purge gas enables the hydrocarbons in the spent purge gas to condense at a higher temperature than without the compressing step, which means that a subsequent cooling step will have to cool the compressed gas less to achieve hydrocarbon condensation.

The INRU compressor 525 can be characterized by a compressor power that is reduced by at least about 10%, alternatively by at least about 20%, or alternatively by at least about 25%, when compared to a compressor power of a compressor in an otherwise similar polymer production system that has either a membrane unit or a PSA unit but not both. The INRU compressor power reduction is primarily due to the smaller INRU compressor recycle stream flow. Retentate stream 710 from the membrane unit (e.g., nitrogen membrane unit) 700 becomes hydrocarbon enriched as nitrogen is permeated through a membrane, therefore additional hydrocarbons could be condensed and pulled out of the INRU system 500, 501. The flow of the remaining vapor streams 820, 821 that are sent to the final purification unit (PSA unit 900 or hydrocarbon membrane unit 950) can be significantly reduced.

One or more recycle streams comprising a purge gas (e.g., nitrogen), hydrocarbons (e.g., isobutane), or both can be introduced to the INRU compressor 525, in addition to the spent purge gas stream 430. The one or more recycle streams can be produced by the INRU system, as will be described in more detail later herein. A volumetric flow to the INRU compressor generally accounts for the spent purge gas stream and the one or more recycle streams introduced to the INRU compressor.

The INRU compressor 525 can have a volumetric flow that is reduced by at least about 20%, alternatively by at least about 25%, or alternatively by at least about 30%, when compared to a volumetric flow to a compressor in an otherwise similar polymer production system comprising an INRU that has either a membrane unit or a PSA unit but not both. While the volumetric flow does not change substantially on the account of the spent purge gas stream volumetric flow, there is a reduction in volumetric flow of the one or more recycle streams introduced to the INRU compressor, owing to recovering more of the purge gas and hydrocarbons from the spent purge gas stream, when compared to an amount of recovered purge gas and hydrocarbons from the spent purge gas stream in an otherwise similar INRU that has either a membrane unit or a PSA unit but not both.

The PEP process 2000 can generally comprise the step 2700 of introducing the compressed gas stream to a first separation unit to produce a first HC stream and a membrane unit feed stream. In an aspect, at least a portion of the compressed gas stream can be cooled prior to the step 2700 of introducing at least a portion of the compressed gas stream to the first separation unit.

At least a portion of the compressed gas stream 526 can be introduced to the first cooling unit 550 to produce a first cooled gas stream 560. The compressed gas stream 526 can be characterized by a temperature of from about 100° F. to about 350° F., alternatively from about 150° F. to about 300° F., or alternatively from about 180° F. to about 275° F. The first cooled gas stream 560 can be characterized by a temperature of from about 50° F. to about 150° F., alternatively from about 75° F. to about 130° F., or alternatively from about 80° F. to about 120° F. A temperature of the first cooled gas stream 560 can be lower than a temperature of the compressed gas stream 526 by from about 50° F. to about 200° F., alternatively from about 75° F. to about 170° F., or alternatively from about 100° F. to about 155° F. Cooling the compressed gas stream promotes the condensation of the hydrocarbons and enables subsequent removal of hydrocarbons from the compressed gas stream. As will be appreciated by one of skill in the art, and with the help of this disclosure, the composition of the compressed gas stream is not affected by cooling it, and as such the composition of the cooled compressed gas stream (e.g., first cooled gas stream 560) is the same as the composition of the compressed gas stream, although some of the components (e.g., hydrocarbons) might change the phase they are present in, for example a component might change from a gas phase in the compressed gas stream to a vapor or liquid phase in the cooled compressed gas stream.

The first cooling unit 550 can comprise any suitable heat exchange unit that can lower the temperature of the compressed gas stream as necessary to promote the condensation on the hydrocarbons in the compressed gas stream 526. The first cooling unit 550 can comprise a heat exchanger wherein the compressed gas stream 526 can exchange heat with a cooling fluid, wherein the temperature of the compressed gas stream 526 is decreased to produce the first cooled gas stream 560, and wherein a temperature of the cooling fluid is increased. Nonlimiting examples of cooling fluids suitable for use in the present disclosure include water, a glycol-water mixture, a salt-water mixture, generic refrigerants, such as propane and propylene, and the like, or combinations thereof.

At least a portion of the first cooled gas stream 560 can be introduced to the first separation unit 600 to produce a first HC stream 610 and a membrane unit feed stream 620. The first separation unit 600 can comprise any suitable vapor-liquid separator that can separate condensed hydrocarbons from the compressed gas stream 526, the first cooled gas stream 560, or both. Nonlimiting examples of vapor-liquid separators suitable for use in the present disclosure include gravity separators, centrifugal separators, filter vane separators, mist eliminator pads, liquid/gas coalescers, and the like, or combinations thereof. The first separation unit 600 can comprise impingement barriers (e.g., mist eliminator pads, plates) that can use inertial impaction to separate condensed hydrocarbons from a gas stream. The gas stream (e.g., the compressed gas stream 526, the first cooled gas stream 560, or both) can follow a tortuous path around these impingement barriers, while liquid droplets (e.g., hydrocarbon liquid droplets) tend to go in straighter paths, impacting these impingement barriers, thereby losing velocity, coalescing, or both, which eventually leads to the liquid droplets falling to a bottom of a separation vessel, such as the first separation unit 600.

The membrane unit feed stream 620 can be collected as a gas stream at a top of the first separation unit 600 (e.g., overhead stream). The membrane unit feed stream 620 can comprise equal to or greater than about 95%, alternatively equal to or greater than about 97%, or alternatively equal to or greater than about 99% of the purge gas (e.g., nitrogen) of the compressed gas stream 526. The membrane unit feed stream 620 can comprise less than about 50%, alternatively less than about 60%, or alternatively less than about 75% of the isobutane of the compressed gas stream 526.

The first hydrocarbon stream 610 can be collected as a liquid stream at a bottom of the first separation unit 600 (e.g., bottoms stream). The first hydrocarbon stream 610 can comprise equal to or greater than about 50%, alternatively equal to or greater than about 60%, or alternatively equal to or greater than about 75% of the isobutane of the compressed gas stream 526. The first hydrocarbon stream 610 can comprise less than about 95%, alternatively less than about 97%, or alternatively less than about 99% of the nitrogen of the compressed gas stream 526. The first hydrocarbon stream 610 can comprise nitrogen in an amount of less than about 5 wt. %, alternatively less than about 2.5 wt. %, or alternatively less than about 1 wt. %, based on the total weight of the first hydrocarbon stream.

At least a portion of the first hydrocarbon stream 610 can be recycled to one or more distillation columns. For example, at least a portion of the first hydrocarbon stream 610 can be recycled to the heavy distillation column 300, for example by adding a portion of the first hydrocarbon stream 610 to the gas stream 210.

At least a portion of the first hydrocarbon stream 610 can be optionally introduced to the first stripping unit 650 to produce a purified first hydrocarbon stream 660 and a third recovered purge gas stream (e.g., third nitrogen stream) 670. The first stripping unit 650 can comprise any suitable stripping column that can remove at least a portion of the purge gas (e.g., nitrogen) from the first hydrocarbon stream 610. Nonlimiting examples of stripping columns suitable for use in the present disclosure include trayed stripping columns, packed stripping columns, flash drums, and the like, or combinations thereof. Generally, stripping columns employ a countercurrent flow of a liquid stream (e.g., first hydrocarbon stream 610) and an inert gas stream (e.g., inert gas, nitrogen, hydrogen, methane, ethane, ethylene), wherein the liquid stream usually flows from the top of the stripping column towards the bottom of the stripping column where it is collected (e.g., purified first hydrocarbon stream 660), and wherein the inert gas stream usually travels from the bottom of the stripping column towards the top of the stripping column where it is collected (e.g., third recovered purge gas stream 670).

An amount of purge gas (e.g., nitrogen) in the purified first hydrocarbon stream 660 can be lower than an amount of purge gas in the first hydrocarbon stream 610. An amount of nitrogen in the purified first hydrocarbon stream 660 can be less than about 90%, alternatively less than about 92.5%, or alternatively less than about 95% of the nitrogen of the first hydrocarbon stream 610. The purified first hydrocarbon stream 660 can comprise nitrogen in an amount of less than about 0.5 wt. %, alternatively less than about 0.25 wt. %, or alternatively less than about 0.1 wt. %, based on the total weight of the purified first hydrocarbon stream.

The purified first hydrocarbon stream 660 can comprise isobutane and other hydrocarbons such as ethane, ethylene, methane, propylene, propane, butane, pentane, hexane, 1-hexene, heavier hydrocarbons. The purified first hydrocarbon stream 660 can comprise isobutane in an amount of equal to or greater than about 85 wt. %, alternatively equal to or greater than about 90 wt. %, or alternatively equal to or greater than about 95 wt. %, based on the total weight of the purified first hydrocarbon stream. The purified first hydrocarbon stream 660 can comprise nitrogen in an amount of less than about 0.1 wt. %, alternatively less than about 0.08 wt. %, or alternatively less than about 0.05 wt. %, based on the total weight of the purified first hydrocarbon stream.

At least a portion of the purified first hydrocarbon stream 660 comprising isobutane 665 can be recycled to one or more distillation columns. For example, at least a portion of the purified first hydrocarbon stream 660 comprising isobutane 665 can be recycled to the heavy distillation column 300, e.g., by adding a portion thereof to the gas stream 210.

The third recovered purge gas stream 670 can comprise nitrogen in an amount of equal to or greater than about 5 wt. %, alternatively equal to or greater than about 10 wt. %, or alternatively equal to or greater than about 15 wt. %, based on the total weight of the third recovered purge gas stream. The third recovered purge gas stream 670 can comprise isobutane in an amount of less than about 80%, alternatively less than about 70%, or alternatively less than about 60%, based on the total weight of the third recovered purge gas stream. At least a portion of the third recovered purge gas stream 670 can be recycled via stream 671 to the INRU compressor 525.

The PEP process 2000 can generally comprise the step 2800 of introducing the membrane unit feed stream to a membrane unit to produce a first recovered purge gas stream and a retentate stream. Optionally, at least a portion of the compressed gas stream can be heated prior to the step 2800 of introducing at least a portion of the membrane unit feed stream to the membrane unit.

At least a portion of the membrane unit feed stream 620 can be optionally introduced to the first membrane unit feed heater 625 to produce a heated membrane unit feed stream 621. The membrane unit feed stream 620 can be characterized by a temperature of from about 50° F. to about 150° F., alternatively from about 75° F. to about 130° F., or alternatively from about 80° F. to about 120° F. The heated membrane unit feed stream 621 can be characterized by a temperature of from about 70° F. to about 170° F., alternatively from about 95° F. to about 150° F., or alternatively from about 100° F. to about 140° F. Without wishing to be limited by theory, heating the membrane unit feed stream can enhance differences in permeability (e.g., permeability with respect to a polymeric selective membrane, such as a nitrogen membrane) between the components of the membrane unit feed stream, e.g., nitrogen and hydrocarbons, such as isobutane. As will be appreciated by one of skill in the art, and with the help of this disclosure, the composition of the membrane unit feed stream is not affected by heating it, and as such the composition of the heated membrane unit feed stream is the same as the composition of the membrane unit feed stream.

The first membrane unit feed heater 625 can comprise any suitable heat exchange unit that can increase the temperature of the membrane unit feed stream as necessary to enhance the separation of the purge gas (e.g., nitrogen) and hydrocarbons (e.g., isobutane) in the membrane unit 700. The first membrane unit feed heater 625 can comprise a heat exchanger wherein the membrane unit feed stream 620 can exchange heat with a heating fluid, wherein the temperature of the membrane unit feed stream 620 is increased to produce the heated membrane unit feed stream 621, and wherein a temperature of the heating fluid is decreased. Nonlimiting examples of heating fluids suitable for use in the present disclosure include hot water, steam, a hot process fluid stream, and the like, or combinations thereof.

At least a portion of the heated membrane unit feed stream 621 and/or membrane unit feed stream 620 can be introduced to the nitrogen membrane unit 700 to produce a first recovered purge gas stream (e.g., first nitrogen stream) 720 and a retentate stream 710. The nitrogen membrane unit 700 can comprise any suitable membrane unit that can separate nitrogen from the rest of the components of the heated membrane unit feed stream 621 and/or membrane unit feed stream 620.

Generally, membrane units can comprise a membrane, such as a polymeric membrane, which is selective to one or more fluid components of a feed stream (e.g., membrane unit feed stream 620, heated membrane unit feed stream 621; hydrocarbon membrane unit feed stream 821, heated hydrocarbon membrane unit feed stream 822). Usually, the feed stream can be a relatively high-pressure (e.g., from about 150 psig (1.03 MPa) to about 400 psig (2.76 MPa)) gas mixture, which can pass along one side of the membrane. One or more components of the feed stream may selectively permeate through the membrane to a permeate side of the membrane. The one or more components of the feed stream that selectively permeate through the membrane can be swept using a gas (e.g., nitrogen in the case of a nitrogen selective membrane; hydrocarbons such as isobutane in the case of a hydrocarbon selective membrane) on the other side of the membrane (e.g., the permeate side of the membrane) to produce a permeate stream (e.g., first recovered purge gas stream, e.g., first nitrogen stream 720 in the case of a nitrogen selective membrane or third hydrocarbon stream 970 in the case of a hydrocarbon selective membrane). Other components of the feed stream may not permeate through the membrane (e.g., nonpermeating components), and can remain on a retentate side of the membrane (e.g., a feed stream side of the membrane) and exit the membrane unit as a retentate stream (e.g., retentate stream 710 comprising hydrocarbons in the case of a nitrogen selective membrane or fifth recovered purge gas stream 960 (i.e., fifth nitrogen stream) comprising nitrogen 965 in the case of a hydrocarbon selective membrane). A pressure difference across the membrane can drive the permeation process.

The membrane unit can separate components of a gas stream based on size exclusion, wherein smaller gaseous components of a gas stream (e.g., nitrogen) can easily pass through the membrane and can be collected as the permeate stream (e.g., first recovered purge gas stream such as first nitrogen stream 720); while larger components of the gas stream (e.g., hydrocarbons, isobutane) cannot permeate through the membrane and can be collected as the retentate stream (e.g., retentate stream 710).

The membrane unit can separate components of a gas stream based on a solubility of components in the polymeric membrane, wherein components that are more soluble in the polymeric membrane can travel across the membrane (e.g., can selectively permeate through the membrane) and can be collected as the permeate stream; while components that are less soluble in the polymeric membrane cannot cross through the membrane and can be collected as the retentate stream. Where the membrane unit (e.g., membrane unit 700) comprises a nitrogen selective membrane that separates components based on solubility, the nitrogen can selectively permeate through the membrane and can be collected as the permeate stream (e.g., first recovered purge gas stream such as first nitrogen stream 720); while components that are less soluble in the nitrogen selective membrane cannot cross through the membrane and can be collected as the retentate stream (e.g., retentate stream 710).

The membrane unit 700 can be heated. Heating the membrane unit can enhance permeability differences between components of a feed stream (e.g., heated membrane unit feed stream 621), allowing for a better component separation. Heating the membrane unit can further prevent hydrocarbon (e.g., isobutane) condensation within the membrane unit. The membrane unit 700 can be heated at a temperature of from about 70° F. to about 170° F., alternatively from about 95° F. to about 155° F., or alternatively from about 100° F. to about 140° F.

The first recovered purge gas stream (e.g., first nitrogen stream) 720 can comprise nitrogen in an amount of equal to or greater than about 30 mol %, alternatively equal to or greater than about 40 mol %, or alternatively equal to or greater than about 50 mol %, based on the total number of moles of the first recovered purge gas stream. The first recovered purge gas stream 720 can comprise hydrocarbons in an amount of less than about 70%, alternatively less than about 60%, or alternatively less than about 50%, based on the total weight of the first recovered purge gas stream.

The first recovered purge gas stream (e.g., first nitrogen stream) 720 can be characterized by a pressure of from about 1 psig to about 50 psig, alternatively from about 1 psig to about 10 psig, alternatively from about 10 psig to about 50 psig, or alternatively from about 30 psig to about 50 psig. As will be appreciated by one of skill in the art, and with the help of this disclosure, the pressure of the first recovered purge gas stream is dependent on the intended use of the first recovered purge gas stream. For example, if the first recovered purge gas stream is sent to vent, then the first recovered purge gas stream can have a pressure of from about 1 psig to about 10 psig. As another example, if the first recovered purge gas stream is recycled to the purge vessel 400, then the first recovered purge gas stream can have a pressure of from about 30 psig to about 50 psig, in which case (i) a gas booster can be used to pressurize the permeate stream (having a pressure of from about 1 psig to about 10 psig) to a pressure of from about 30 psig to about 50 psig; (ii) the permeate stream can be set to have a pressure of from about 30 psig to about 50 psig (which may require larger membrane area); or both.

At least a portion of the first recovered purge gas stream (e.g., first nitrogen stream) 720 can be introduced to the splitter 730 to produce a first portion 735 of the first purge gas stream (e.g., nitrogen recycle stream) and a second portion 736 of the first purge gas stream comprising low pressure purge gas (e.g., low pressure nitrogen) 737. The splitter 730 can comprise any suitable gas splitter, such as for example a gas splitter valve. The first portion 735 of the first purge gas stream can be recycled to the INRU compressor 525, for example via a nitrogen recycle stream. The second portion 736 of the first purge gas stream can be recycled to a purge vessel, such as the purge vessel 400, for example by introducing the second portion 736 to the middle of the purge vessel 400 (e.g., about mid-way through the height of the purge vessel). The low pressure nitrogen 737 can be characterized by a pressure of from about 25 psig to about 60 psig, alternatively from about 30 psig to about 55 psig, or alternatively from about 30 psig to about 50 psig.

The retentate stream 710 can comprise less than about 30%, alternatively less than about 20%, alternatively less than about 10% of the purge gas of the membrane unit feed stream 620 (or heated stream 621). As will be appreciated by one of skill in the art, and with the help of this disclosure, the amount of nitrogen retained in the retentate stream depends on a variety pf process factors, such as for example a membrane area of the membrane used in the membrane unit 700.

The retentate stream 710 can comprise nitrogen in an amount of less than about 40%, alternatively less than about 30%, or alternatively less than about 20%, based on the total weight of the retentate stream. The retentate stream 710 can comprise isobutane in an amount of equal to or greater than about 40 wt. %, alternatively equal to or greater than about 50 wt. %, or alternatively equal to or greater than about 60 wt. %, based on the total weight of the retentate stream.

The retentate stream 710 can have a hydrocarbon dew point that is greater than a hydrocarbon dew point of the membrane unit feed stream 620 (or heated stream 621). A hydrocarbon dew point generally refers to a temperature at which the hydrocarbon(s) will condense at a certain pressure. Without wishing to be limited by theory, by removing a portion of the purge gas from the membrane unit feed stream, the hydrocarbons in the resulting retentate stream will condense at a higher temperature, when compare to the temperature at which the hydrocarbons in the membrane unit feed stream would condense, thereby allowing for less cooling of the retentate stream to achieve hydrocarbon condensation.

The PEP process 2000 can generally comprise the step 2900 of introducing the retentate stream to a second separation unit to produce a second HC stream and a PSA unit feed stream. At least a portion of the retentate stream can be cooled prior to the step 2900 of introducing at least a portion of the retentate stream to a second separation unit.

At least a portion of the retentate stream 710 can be introduced to the second cooling unit 750 to produce a second cooled gas stream 760. The retentate stream 710 can be characterized by a temperature of from about 70° F. to about 170° F., alternatively from about 95° F. to about 155° F., or alternatively from about 100° F. to about 140° F. The second cooled gas stream 760 can be characterized by a temperature of from about −20° F. to about 110° F., alternatively from about 32° F. to about 100° F., or alternatively from about 40° F. to about 90° F. A temperature of the second cooled gas stream 760 can be lower than a temperature of the retentate stream 710 by from about 90° F. to about 60° F., alternatively from about 63° F. to about 55° F., or alternatively from about 60° F. to about 50° F. Cooling the retentate stream promotes the condensation of the hydrocarbons and enables subsequent removal of hydrocarbons from the retentate stream. As will be appreciated by one of skill in the art, and with the help of this disclosure, the composition of the retentate stream is not affected by cooling it, and as such the composition of the cooled retentate stream (e.g., second cooled gas stream 760) is the same as the composition of the retentate stream, although some of the components (e.g., hydrocarbons) might change the phase they are present in, for example a component might change from a gas phase in the retentate stream to a vapor or liquid phase in the cooled retentate stream.

The second cooling unit 750 can comprise any suitable heat exchange unit that can lower the temperature of the retentate stream as necessary to promote the condensation on the hydrocarbons in the retentate stream 710. The second cooling unit 750 can comprise a heat exchanger wherein the retentate stream 710 can exchange heat with a cooling fluid, wherein the temperature of the retentate stream 710 is decreased to produce the second cooled gas stream 760, and wherein a temperature of the cooling fluid is increased. Nonlimiting examples of cooling fluids suitable for use in the present disclosure include water, a glycol-water mixture, a salt-water mixture, generic refrigerants such as propane and propylene, and the like, or combinations thereof.

At least a portion of the second cooled gas stream 760 can be introduced to the second separation unit 800 to produce a second HC stream 810 and a PSA unit feed stream 820 (or alternatively a hydrocarbon membrane unit feed stream 821 as described in more detail herein with reference to FIG. 1C). The second separation unit 800 can comprise any suitable vapor-liquid separator that can separate condensed hydrocarbons from the retentate stream 710, the second cooled gas stream 760, or both. In some aspects, the second separation unit 800 can comprise any suitable vapor-liquid separator that was described previously herein for the first separation unit 600.

The PSA unit feed stream 820 can be collected as a gas stream at a top of the second separation unit 800 (e.g., overhead stream). The PSA unit feed stream 820 can comprise equal to or greater than about 97%, alternatively equal to or greater than about 99%, or alternatively equal to or greater than about 99.9% of the purge gas (e.g., nitrogen) of the retentate stream 710. The PSA unit feed stream 820 can comprise less than about 45%, alternatively less than about 35%, or alternatively less than about 25% of the isobutane of the retentate stream 710.

The PSA unit feed stream 820 can be characterized by a pressure of from about 150 psig to about 300 psig, alternatively from about 180 psig to about 270 psig, or alternatively from about 210 psig to about 240 psig.

The second hydrocarbon stream 810 can be collected as a liquid stream at a bottom of the second separation unit 800 (e.g., bottoms stream). The second hydrocarbon stream 810 can comprise equal to or greater than about 55%, alternatively equal to or greater than about 65%, or alternatively equal to or greater than about 75% of the isobutane of the retentate stream 710. The second hydrocarbon stream 810 can comprise less than about 97%, alternatively less than about 99%, or alternatively less than about 99.9% of the nitrogen of the retentate stream 710. The second hydrocarbon stream 810 can comprise nitrogen in an amount of less than about 5 wt. %, alternatively less than about 2.5 wt. %, or alternatively less than about 1 wt. %, based on the total weight of the second hydrocarbon stream.

At least a portion of the second hydrocarbon stream 810 can be recycled to one or more distillation columns. For example, at least a portion of the second hydrocarbon stream 810 can be recycled to the heavy distillation column 300, for example via addition of a portion thereof to the gas stream 210.

At least a portion of the second hydrocarbon stream 810 can be optionally introduced to the second stripping unit 850 to produce a purified second hydrocarbon stream 860 and a fourth recovered purge gas stream (e.g., fourth nitrogen stream) 870. The second stripping unit 850 can comprise any suitable stripping column that can remove at least a portion of the purge gas (e.g., nitrogen) from the second hydrocarbon stream 810. The second stripping unit 850 can comprise any suitable stripping column that was described previously herein for the first stripping unit 650.

An amount of purge gas in the purified second hydrocarbon stream 860 can be lower than an amount of purge gas in the second hydrocarbon stream 810. An amount of nitrogen in the purified second hydrocarbon stream 860 can be less than about 90%, alternatively less than about 92.5%, or alternatively less than about 95% of the nitrogen of the second hydrocarbon stream 810. The purified second hydrocarbon stream 860 can comprise nitrogen in an amount of less than about 0.5 wt. %, alternatively less than about 0.25 wt. %, or alternatively less than about 0.1 wt. %, based on the total weight of the purified second hydrocarbon stream.

The purified second hydrocarbon stream 860 can comprise isobutane and other hydrocarbons such as ethane, ethylene, methane, propylene, propane, butane, pentane, hexane, 1-hexene, heavier hydrocarbons. The purified second hydrocarbon stream 860 can comprise isobutane in an amount of equal to or greater than about 85 wt. %, alternatively equal to or greater than about 90 wt. %, or alternatively equal to or greater than about 95 wt. %, based on the total weight of the purified second hydrocarbon stream. The purified second hydrocarbon stream 860 can comprise nitrogen in an amount of less than about 0.1 wt. %, alternatively less than about 0.08 wt. %, or alternatively less than about 0.05 wt. %, based on the total weight of the purified second hydrocarbon stream.

At least a portion of the purified second hydrocarbon stream 860 comprising isobutane 865 can be recycled to one or more distillation columns. For example, at least a portion of the purified second hydrocarbon stream 860 comprising isobutane 865 can be recycled to the heavy distillation column 300, e.g., via addition of a portion thereof to the gas stream 210.

The fourth recovered purge gas stream 870 can comprise nitrogen in an amount of equal to or greater than about 5 wt. %, alternatively equal to or greater than about 10 wt. %, or alternatively equal to or greater than about 15 wt. %, based on the total weight of the fourth recovered purge gas stream. The fourth recovered purge gas stream 870 can comprise isobutane in an amount of less than about 80%, alternatively less than about 70%, or alternatively less than about 60%, based on the total weight of the fourth recovered purge gas stream. At least a portion of the fourth recovered purge gas stream 870 can be recycled via stream 871 to the INRU compressor 525.

The first stripping unit 650 and the second stripping unit 850 can be different stripping units. Alternatively, the first stripping unit 650 and the second stripping unit 850 can be the same stripping unit (i.e., a common stripping unit), and the first hydrocarbon stream 610 and the second hydrocarbon stream 810 can be combined prior to introducing to the common stripping unit, wherein a single purified hydrocarbon stream and a single recovered purge gas stream are recovered from the common stripping unit.

Where a common stripping unit is employed, the single purified hydrocarbon stream can comprise isobutane and other hydrocarbons such as ethane, ethylene, methane, propylene, propane, butane, pentane, hexane, 1-hexene, heavier hydrocarbons. The single purified hydrocarbon stream can comprise isobutane in an amount of equal to or greater than about 85 wt. %, alternatively equal to or greater than about 90 wt. %, or alternatively equal to or greater than about 95 wt. %, based on the total weight of the purified second hydrocarbon stream. The single purified hydrocarbon stream can comprise nitrogen in an amount of less than about 0.1 wt. %, alternatively less than about 0.08 wt. %, or alternatively less than about 0.05 wt. %, based on the total weight of the single purified hydrocarbon stream. At least a portion of the single purified hydrocarbon stream comprising isobutane can be recycled to one or more distillation columns.

Where a common stripping unit is employed, the single recovered purge gas stream can comprise nitrogen in an amount of equal to or greater than about 5 wt. %, alternatively equal to or greater than about 10 wt. %, or alternatively equal to or greater than about 15 wt. %, based on the total weight of the single recovered purge gas stream. The single recovered purge gas stream can comprise isobutane in an amount of less than about 80%, alternatively less than about 70%, or alternatively less than about 60%, based on the total weight of the single recovered purge gas stream. At least a portion of the single recovered purge gas stream can be recycled to the INRU compressor 525.

The PEP process 2000 can generally comprise the step 2950 of introducing the purification unit feed stream (e.g., PSA unit feed stream) to a PSA unit to produce a second recovered purge gas stream and a tail gas stream.

As shown in FIG. 1B, at least a portion of the PSA unit feed stream 820 can be introduced to the PSA unit 900 to produce the second recovered purge gas stream 910 and the tail gas stream 920. The PSA unit 900 can comprise any suitable PSA unit that can enable separation of a purge gas (e.g., nitrogen) from hydrocarbons (e.g., isobutane). Generally, the PSA unit 900 can comprise a PSA adsorber (e.g., hydrocarbon adsorber) that selectively adsorbs hydrocarbons while allowing smaller nonpolar molecules such as purge gas molecules (e.g., nitrogen molecules) to flow past the adsorber and be collected. PSA units generally operate at ambient temperature. The PSA unit feed stream 820 can be introduced to the PSA unit 900 at a first pressure during an adsorption step, wherein the hydrocarbons of the PSA unit feed stream diffuse into pores of the hydrocarbon adsorber and are adsorbed therein, while the purge gas of the PSA unit feed stream travels through the PSA unit without being adsorbed by the hydrocarbon adsorber and can be recovered as the second recovered purge gas stream 910. When the hydrocarbon adsorber becomes saturated with hydrocarbons, the PSA unit switches from the adsorption step to a regeneration step. During the regeneration step, the PSA unit 900 is depressurized (e.g., brought to a second pressure, wherein the second pressure is lower than the first pressure) to promote the desorption of hydrocarbons from the hydrocarbon adsorber. A sweeping gas can be introduced to the PSA unit 900 to desorb hydrocarbons, remove (e.g., sweep away) the desorbed hydrocarbons, or both, thereby producing the tail gas stream, wherein the tail gas stream can comprise at least a portion of the sweeping gas and at least a portion of the desorbed hydrocarbons. The sweeping gas can comprise isobutane, such as for example isobutane produced by one or more distillation columns, such as the one or more distillation columns in the PEP system 1000, as previously described herein. A purge step can follow the regeneration step, wherein the PSA unit can be purged and returned to the first pressure prior to the subsequent adsorption step. Generally, a PSA process is conducted with at least 2 PSA units running in parallel, wherein one of the PSA units is undergoing the adsorption step, while the other PSA unit is undergoing the regeneration step. At any given time, there should be a PSA unit either undergoing the adsorption step or ready to undergo the adsorption step, thereby providing for a continuous process. Nonlimiting examples of hydrocarbon adsorbers (e.g., hydrocarbon adsorbents) suitable for use in the present disclosure include molecular sieves, zeolites, silica gel, activated carbon, and the like, or combinations thereof.

The INRU 500 can comprise from about 2 to about 8 pressure swing adsorption units operated in parallel, alternatively from about 3 to about 7 pressure swing adsorption units operated in parallel, or alternatively from about 4 to about 6 pressure swing adsorption units operated in parallel. For example, the PSA unit 900 as shown in FIG. 1B comprises at least two PSA units working in parallel.

The PSA unit 900 can be characterized by a first pressure of from about 150 psig to about 300 psig, alternatively from about 180 psig to about 270 psig, or alternatively from about 210 psig to about 240 psig. The PSA unit 900 can be characterized by a second pressure of from about 2 psig to about 20 psig, alternatively from about 3 psig to about 15 psig, or alternatively from about 4 psig to about 10 psig. A difference between the first pressure and the second pressure in the PSA unit 900 can be from about 148 psig to about 280 psig, alternatively from about 177 psig to about 255 psig, or alternatively from about 206 psig to about 230 psig.

The PSA unit 900 can be characterized by a cycle time of from about 1 minute to about 60 minutes, alternatively from about 2 minutes to about 50 minutes, alternatively from about 2.5 minutes to about 40 minutes, or alternatively from about 5 minutes to about 20 minutes. For purposes of the disclosure herein, the cycle time of the PSA unit can be defined as the time between the start of two successive adsorption steps, e.g., a time frame necessary to complete an adsorption step, a desorption step and a purging step that are consecutive.

The PSA unit 900 can be characterized by a cycle time that is increased by at least about 50%, alternatively by at least 60%, or alternatively by at least 75%, when compared to a cycle time of a PSA unit in an otherwise similar polymer production system that lacks a membrane unit, such as membrane unit 700. The use of the membrane unit 700 in the PEP system 1000 allows for the removal of more hydrocarbons from the PSA unit feed stream, and as such the PSA unit can run the adsorption step for a longer time period, as there is a smaller amount of hydrocarbons in the PSA unit feed stream to be adsorbed by the hydrocarbon adsorber.

The PSA unit feed stream 820 can be reduced by at least about 40%, alternatively by at least 50%, or alternatively by at least 60%, when compared to a PSA unit feed stream in an otherwise similar polymer production system that lacks a membrane unit. The use of the membrane unit 700 in the PEP system 1000 allows for the removal of more hydrocarbons from the PSA unit feed stream, thereby leading to a smaller amount of PSA unit feed stream being introduced to the PSA unit 900.

The second recovered purge gas stream (e.g., second nitrogen stream) 910 can comprise nitrogen in an amount of equal to or greater than about 85 mol %, alternatively equal to or greater than about 90 mol %, or alternatively equal to or greater than about 95 mol %, based on the total number of moles of the second recovered purge gas stream. A molar concentration of purge gas in the second recovered purge gas stream 910 can be greater than a molar concentration of purge gas in the first recovered purge gas stream 720. Generally, PSA separation processes can produce more pure products than membrane separation processes.

The second recovered purge gas stream 910 can comprise isobutane in an amount of less than about 0.1%, alternatively less than about 0.08%, or alternatively less than about 0.05%, based on the total weight of the second recovered purge gas stream.

At least a portion of the second recovered purge gas stream 910 comprising nitrogen 915 can be recycled to a purge vessel, such as the purge vessel 400, e.g., via stream 509 and the purge gas stream 410 as shown in FIG. 1A.

The tail gas stream 920 can comprise isobutane in an amount of equal to or greater than about 25%, alternatively equal to or greater than about 30%, or alternatively equal to or greater than about 35%, based on the total weight of the tail gas stream. An amount of isobutane in the tail gas stream 920 is greater than an amount of isobutane in the PSA unit feed stream 820. PSA produces high purity nitrogen (e.g., stream 910) by removing the nitrogen from the PSA unit feed stream 820, and as such the tail gas stream will have less nitrogen and more other components, such as hydrocarbons. Further, when the sweeping gas comprises isobutane, the isobutane content of the tail gas will be relatively high. At least a portion of the tail gas stream 920 can be recycled to the INRU compressor 525.

The PEP process 2000 can generally comprise the step 2975 of introducing the purification unit feed stream (e.g., HC membrane unit feed stream) to a HC membrane unit to produce a third HC stream and a fifth recovered purge gas stream.

In an alternative aspect as shown in INRU 501 of FIG. 1C, the PEP process 2000 can generally comprise a step of introducing a hydrocarbon membrane unit feed stream to a hydrocarbon membrane unit to produce a third hydrocarbon stream and a fifth recovered purge gas stream. In such aspect, the hydrocarbon membrane unit can replace the PSA unit 900 in the INRU 500. Optionally, at least a portion of the hydrocarbon membrane unit feed stream can be heated prior to the step of introducing at least a portion of the hydrocarbon membrane unit feed stream to the hydrocarbon membrane unit. For purposes of the disclosure herein, the "PSA unit feed stream" 820 and the "HC membrane unit feed stream" 821 are the same stream (e.g., with the same composition) emitted from the second separation unit 800, wherein the stream is designated with a different name and stream number based on the intended destination of the stream: if the stream is communicated to the PSA unit 900, then the stream is designated "PSA unit feed stream" 820; and if the stream is communicated to the HC membrane unit 950, then the stream is designated "HC membrane unit feed stream" 821.

Referring to FIG. 1C, in some configurations of the INRU 501, at least a portion of the hydrocarbon membrane unit feed stream 821 can be optionally introduced to the second membrane unit feed heater 825 to produce a heated hydrocarbon membrane unit feed stream 822. The hydrocarbon membrane unit feed stream 821 can be characterized by a temperature of from about −20° F. to about 110° F., alternatively from about 32° F. to about 100° F., or alternatively from about 40° F. to about 90° F. The heated hydrocarbon membrane unit feed stream 822 can be characterized by a temperature of from about 70° F. to about 110° F., alternatively from about 80° F. to about 105° F., or alternatively from about 90° F. to about 100° F. Without wishing to be limited by theory, for configurations where the hydrocarbon membrane unit feed stream is heated, heating the hydrocarbon membrane unit feed stream can enhance differences in permeability (e.g., permeability with respect to a polymeric selective membrane, such as a hydrocarbon membrane) between the components of the membrane unit feed stream, e.g., nitrogen and hydrocarbons, such as isobutane. As will be appreciated by one of skill in the art, and with the help of this disclosure, the composition of the hydrocarbon membrane unit feed stream is not affected by heating it, and as such the composition of the heated hydrocarbon membrane unit feed stream is the same as the composition of the hydrocarbon membrane unit feed stream.

In other configurations of the INRU 501, at least a portion of the hydrocarbon membrane unit feed stream 821 can be introduced to the hydrocarbon membrane unit 950 without heating the hydrocarbon membrane unit feed stream 821. In such configurations, and without wishing to be limited by theory, heavier hydrocarbons can permeate through the hydrocarbon membrane, leaving the retentate stream lighter, which can in turn decrease a dew point of the retentate stream. Further, without wishing to be limited by theory, since colder temperatures can suppress light gas (such as $N_2$, $H_2$, etc.) diffusivity, and thus permeability through the membrane, leaving the hydrocarbon membrane unit feed stream 821 un-heated may enhance the selectivity between hydrocarbons and light gas streams.

The second membrane unit feed heater 825 can comprise any suitable heat exchange unit that can increase the temperature of the hydrocarbon membrane unit feed stream as necessary to enhance the separation of the purge gas (e.g., nitrogen) and hydrocarbons (e.g., isobutane) in the hydrocarbon membrane unit 950. The second membrane unit feed heater 825 can comprise a heat exchanger wherein the hydrocarbon membrane unit feed stream 821 can exchange heat with a heating fluid, wherein the temperature of the hydrocarbon membrane unit feed stream 821 is increased to produce the heated hydrocarbon membrane unit feed stream 822, and wherein a temperature of the heating fluid is decreased. Nonlimiting examples of heating fluids suitable for use in the present disclosure include hot water, steam, a hot process fluid stream, and the like, or combinations thereof.

At least a portion of the heated hydrocarbon membrane unit feed stream 822 and/or the hydrocarbon membrane unit feed stream 821 can be introduced to the hydrocarbon membrane unit 950 to produce a fifth recovered purge gas stream (e.g., fifth nitrogen stream) 960 (e.g., a high purity nitrogen stream) and a third hydrocarbon stream 970. The hydrocarbon membrane unit 950 can comprise any suitable membrane unit that can separate hydrocarbons from the rest of the components (e.g., purge gas, nitrogen) of the heated hydrocarbon membrane unit feed stream 822 and/or the hydrocarbon membrane unit feed stream 821.

The hydrocarbon membrane unit 950 can comprise a hydrocarbon selective membrane. A nonlimiting example of a hydrocarbon selective membrane includes VAPORSEP membranes, which are commercially available from Membrane Technology & Research. Where the membrane unit (e.g., hydrocarbon membrane unit 950) comprises a hydrocarbon selective membrane that separates components based on solubility, the hydrocarbons can selectively permeate through the membrane and can be collected as the permeate stream (e.g., third hydrocarbon stream 970); while components that are less soluble in the hydrocarbon selective membrane cannot cross through the membrane and can be collected as the retentate stream (e.g., fifth recovered purge gas stream, fifth nitrogen stream 960).

In some configurations of the INRU 501, the hydrocarbon membrane unit 950 is not heated.

In other configurations of the INRU 501, the hydrocarbon membrane unit 950 can be heated. In such configurations, heating the hydrocarbon membrane unit 950 can enhance permeability differences between components of a feed stream (e.g., hydrocarbon membrane unit feed stream 821, heated hydrocarbon membrane unit feed stream 822), allowing for a better component separation. Heating the hydrocarbon membrane unit 950 can further prevent hydrocarbon (e.g., isobutane) condensation within the membrane unit. The hydrocarbon membrane unit 950 can be heated at a temperature of from about 70° F. to about 110° F., alternatively from about 80° F. to about 105° F., or alternatively from about 90° F. to about 100° F.

The fifth recovered purge gas stream (e.g., fifth nitrogen stream) 960 can comprise nitrogen in an amount of equal to or greater than about 85 mol %, alternatively equal to or greater than about 90 mol %, or alternatively equal to or greater than about 95 mol %, based on the total number of moles of the fifth recovered purge gas stream.

The fifth recovered purge gas stream 960 can comprise hydrocarbons in an amount of less than about 5%, alternatively less than about 3%, or alternatively less than about 2%, based on the total weight of the fifth recovered purge gas stream. The fifth recovered purge gas stream 960 can comprise less than about 15%, alternatively less than about 12%, or alternatively less than about 10% of the hydrocarbons (e.g., isobutane) of the hydrocarbon membrane unit feed stream 821.

At least a portion of the fifth recovered purge gas stream (e.g., fifth nitrogen stream) 960 comprising nitrogen 965 can be recycled to a purge vessel, such as the purge vessel 400, e.g., via stream 509 and the purge gas stream 410 as shown in FIG. 1A. In some configurations, at least a portion of the fifth recovered purge gas stream 960 can be introduced to the middle of the purge vessel 400 (e.g., about mid-way through the height of the purge vessel).

The third hydrocarbon stream 970 can comprise hydrocarbons (e.g., isobutane) in an amount of equal to or greater than about 40 wt. %, alternatively equal to or greater than about 50 wt. %, or alternatively equal to or greater than about 55 wt. %, based on the total weight of the third hydrocarbon stream. The third hydrocarbon stream 970 can comprise nitrogen in an amount of less than about 45%, alternatively less than about 50%, or alternatively less than about 60%, based on the total weight of the third hydrocarbon stream.

In some configurations, at least a portion of the third hydrocarbon stream 970 can be recycled to the INRU compressor 525.

The various embodiments shown in the Figures can be simplified and may not illustrate common equipment such as heat exchangers, pumps, and compressors; however, a skilled artisan would recognize the disclosed processes and systems may include such equipment commonly used throughout polymer manufacturing.

A skilled artisan will recognize that industrial and commercial polyethylene manufacturing processes can necessitate one or more, often several, compressors or similar apparatuses. Such compressors are used throughout polyethylene manufacturing, for example to pressurize reactors 104, 106 during polymerization. Further, a skilled artisan will recognize that a polyethylene manufacturing process includes one or more deoxygenators, similar de-oxidizing apparatuses, or both, for instance for purifying solvents or reactants, for purging reactors of oxygen, or both. Because the infrastructure and the support therefore, for example to provide power and maintain the compressors, deoxygenators, or both already exists within a commercial polyethylene manufacturing plant, reallocating a portion of these available resources for use in the disclosed systems can necessitate little, if any, additional capital expenditure in order to incorporate the disclosed systems and or processes.

Further, because compressors, deoxygenators, and various other components are already employed in various polyethylene processes and systems, the opportunity for increased operation of such apparatuses can improve the overall efficiency of polyethylene production systems and processes. For example, when a portion of a PEP process or system is taken off-line for maintenance, repair, or both other portions of the system (e.g., a compressor, a deoxygenator, a reactor, etc.) can continue to provide service according to the current processes. Operating, reallocating resources, or both for operation of the disclosed PEP systems, PEP processes, or both can thereby increase the efficiency with which conventional systems are used.

According to the present disclosure, a process for ethylene polymerization can generally comprise the steps of (a) polymerizing ethylene in a loop slurry reactor system to obtain a polymerization product stream; (b) separating at least a portion of the polymerization product stream in a flash chamber into a gas stream and a polymer stream comprising polyethylene, isobutane, ethylene and ethane; (c) introducing at least a portion of the gas stream to one or more distillation columns to produce isobutane; (d) contacting at least a portion of the polymer stream with nitrogen in a purge vessel to yield a purged polymer stream and a spent nitrogen stream, wherein the purged polymer stream comprises polyethylene, and wherein the spent nitrogen comprises nitrogen, isobutane, ethylene, and ethane; (e) introducing at least a portion of the spent nitrogen stream to a compressor to produce a compressed gas stream, wherein the compressed gas stream has a pressure of from about 200 psig to about 400 psig; (f) introducing at least a portion of the compressed gas stream to a first separation unit comprising a vapor-liquid separator to produce a first hydrocarbon stream and a nitrogen membrane unit feed stream, wherein the first hydrocarbon stream comprises equal to or greater than about 50% of the isobutane of the compressed gas stream, and wherein the nitrogen membrane unit feed stream comprises equal to or greater than about 95% of the nitrogen of the compressed gas stream; (g) introducing at least a portion of the nitrogen membrane unit feed stream to a nitrogen membrane unit comprising a nitrogen selective membrane to produce a first recovered nitrogen stream and a retentate stream, wherein the retentate stream comprises less than about 30% of the nitrogen of the nitrogen membrane unit feed stream, and wherein the retentate stream comprises equal to or greater than about 90% of the isobutane of the nitrogen membrane unit feed stream; (h) recycling a first portion of the first recovered nitrogen stream to the compressor; (i) recycling a second portion of the first recovered nitrogen stream to the purge vessel; (j) introducing at least a portion of the retentate stream to a second separation unit comprising a vapor-liquid separator to produce a second hydrocarbon stream and a pressure swing adsorption (PSA) unit feed stream, wherein the PSA unit feed stream comprises equal to or greater than about 97% of the nitrogen of the retentate stream; (k) introducing at least a portion of the first hydrocarbon stream, at least a portion of the second hydrocarbon stream, or both to a nitrogen stripping unit to produce a purified hydrocarbon stream and a third recovered nitrogen stream; (l) recycling at least a portion of the purified hydrocarbon stream to the one or more distillation columns; (m) recycling at least a portion of the third recovered nitrogen stream to the compressor; (n) introducing at least a portion of the PSA unit feed stream to a PSA unit to produce a second recovered nitrogen stream and a tail gas stream, wherein a molar concentration of nitrogen in the second recovered nitrogen stream is greater than a molar concentration of nitrogen in the first recovered nitrogen stream; (o) recycling at least a portion of the second recovered nitrogen stream to the purge vessel; and (p) recycling at least a portion of the tail gas stream to the compressor. The compressor can have a volumetric flow that is reduced by at least about 20% when compared to a volumetric flow to a compressor in an otherwise similar polymer production system that has either a nitrogen selective membrane unit or a PSA unit but not both.

According to the present disclosure, a process for ethylene polymerization can generally comprise the steps of (a) polymerizing ethylene in a loop slurry reactor system to obtain a polymerization product stream; (b) separating at least a portion of the polymerization product stream in a flash chamber into a gas stream and a polymer stream comprising polyethylene, isobutane, ethylene and ethane; (c) introducing at least a portion of the gas stream to one or more distillation columns to produce isobutane; (d) contacting at least a portion of the polymer stream with nitrogen in a purge vessel to yield a purged polymer stream and a spent nitrogen stream, wherein the purged polymer stream comprises polyethylene, and wherein the spent nitrogen comprises nitrogen, isobutane, ethylene, and ethane; (e) introducing at least a portion of the spent nitrogen stream to a compressor to produce a compressed gas stream, wherein the compressed gas stream has a pressure of from about 200 psig to about 400 psig; (f) introducing at least a portion of the compressed gas stream to a first separation unit comprising a vapor-liquid separator to produce a first hydrocarbon stream and a nitrogen membrane unit feed stream, wherein the first hydrocarbon stream comprises equal to or greater than about 50% of the isobutane of the compressed gas stream, and wherein the nitrogen membrane unit feed stream comprises equal to or greater than about 95% of the nitrogen of the compressed gas stream; (g) introducing at least a portion of the nitrogen membrane unit feed stream to a nitrogen membrane unit comprising a nitrogen selective membrane to produce a first recovered nitrogen stream and a retentate stream, wherein the retentate stream comprises less than about 30% of the nitrogen of the nitrogen membrane unit feed stream, and wherein the retentate stream comprises equal to or greater than about 90% of the isobutane of the nitrogen membrane unit feed stream; (h) recycling a first portion of the first recovered nitrogen stream to the compressor; (i) recycling a second portion of the first recovered nitrogen stream to the purge vessel; (j) introducing at least a portion of the retentate stream to a second separation unit comprising a vapor-liquid separator to produce a second hydrocarbon stream and a hydrocarbon membrane unit feed stream, wherein the hydrocarbon membrane unit feed stream comprises equal to or greater than about 97% of the nitrogen of the retentate stream; (k) introducing at least a portion of the first hydrocarbon stream, at least a portion of the second hydrocarbon stream, or both to a nitrogen stripping unit to produce a purified hydrocarbon stream and a third recovered nitrogen stream; (l) recycling at least a portion of the purified hydrocarbon stream to the one or more distillation columns; (m) recycling at least a portion of the third recovered nitrogen stream to the compressor; (n) introducing at least a portion of the hydrocarbon membrane unit feed stream to a hydrocarbon membrane unit comprising a hydrocarbon selective membrane to produce a fifth recovered nitrogen stream and a third hydrocarbon stream; (o) recycling at least a portion of the fifth recovered nitrogen stream to the compressor; and (p) recycling at least a portion of the third hydrocarbon stream to the one or more distillation columns. The compressor can have a volumetric flow that is reduced by at least about 5%, alternatively by at least about 7.5%, or alternatively by at least about 10% when compared to a volumetric flow to a compressor in an otherwise similar polymer production system that has either a nitrogen selective membrane unit or a hydrocarbon selective membrane unit but not both.

According to the present disclosure, an isobutane and nitrogen recovery unit (INRU) system can comprise a compressor, a first cooling unit, a first separation unit, first stripping unit, a nitrogen membrane unit, a second cooling unit, a second separation unit, second stripping unit, and a pressure swing adsorption (PSA) unit; wherein the compressor is configured to receive a spent purge gas stream, a nitrogen recycle stream, and a tail gas stream, and to produce a compressed gas stream; wherein the compressor has a volumetric flow that is reduced by at least about 20% when compared to a volumetric flow to a compressor in an otherwise similar INRU system that has either a hydrocarbon membrane unit or a PSA unit but not both; wherein the first cooling unit is configured to receive at least a portion of the compressed gas stream prior to introducing at least a portion of the compressed gas stream to the first separation unit; wherein the first separation unit is a vapor-liquid separator configured to receive at least a portion of the compressed gas stream, and to produce a first hydrocarbon stream and a nitrogen membrane unit feed stream, wherein the first hydrocarbon stream is a liquid stream, and wherein the nitrogen membrane unit feed stream is a gaseous stream; wherein the first stripping unit is configured to receive at least a portion of the first hydrocarbon stream, and to produce a purified first hydrocarbon stream and a third nitrogen stream; wherein the nitrogen membrane unit is configured to receive at least a portion of the nitrogen membrane unit feed stream, and to produce a first nitrogen stream and a retentate stream, wherein the nitrogen membrane unit has a nitrogen selective membrane disposed therein, wherein the nitrogen selective membrane allows nitrogen to pass through and be collected as a permeate stream (e.g., first nitrogen stream), wherein the nitrogen selective membrane does not allow hydrocarbons to pass through (although some lighter hydrocarbons could permeate through the nitrogen selective membrane, and as such at least a portion of the first nitrogen stream can be recycled back to the INRU compressor to recover such lighter hydrocarbons that could permeate through the nitrogen selective membrane), wherein hydrocarbons can be collected as the retentate stream, wherein the first nitrogen stream has a pressure of from about 1 psig to about 50 psig, wherein the nitrogen recycle stream comprises at least a portion of the first nitrogen stream, and wherein the retentate stream has a hydrocarbon dew point that is greater than a hydrocarbon dew point of the membrane unit feed stream; wherein the second cooling unit is configured to receive at least a portion of the retentate stream prior to introducing at least a portion of the retentate stream to the second separation unit; wherein the second separation unit is a vapor-liquid separator configured to receive at least a portion of the retentate stream, and to produce a second hydrocarbon stream and a PSA unit feed stream, wherein the second hydrocarbon stream is a liquid stream, wherein the PSA unit feed stream is a gaseous stream, and wherein the PSA unit feed stream comprises hydrocarbons and nitrogen; wherein the second stripping unit is configured to receive at least a portion of the second hydrocarbon stream, and to produce a purified second hydrocarbon stream and a fourth nitrogen stream; and wherein the PSA unit is configured to receive at least a portion of the PSA unit feed stream, and to produce a second nitrogen stream and the tail gas stream, wherein the PSA unit has a PSA adsorber disposed therein, wherein the PSA adsorber allows the nitrogen to pass through the PSA unit and be collected as the second nitrogen stream, wherein the PSA adsorber adsorbs the hydrocarbons, and wherein a sweeping gas stream comprising nitrogen desorbs the hydrocarbons from the PSA adsorber to produce the tail gas stream. In some configurations of the INRU system disclosed herein, the first nitrogen stream can be combined with the second nitrogen stream (e.g., high purity nitrogen) from the PSA unit to form a medium purity nitrogen purge gas stream. The medium purity nitrogen purge gas stream could be further recycled to a purge vessel, such as the purge vessel 400, for example via the purge gas stream 410 (e.g., via the recycle stream 509 as shown in FIG. 1A).

According to the present disclosure, an isobutane and nitrogen recovery unit (INRU) system can comprise a compressor, a first cooling unit, a first separation unit, first stripping unit, a nitrogen membrane unit, a second cooling unit, a second separation unit, second stripping unit, and a hydrocarbon membrane unit; wherein the compressor is configured to receive a spent purge gas stream, a nitrogen recycle stream, and a tail gas stream, and to produce a compressed gas stream; wherein the compressor has a volumetric flow that is reduced by at least about 5%, alternatively by at least about 7.5%, or alternatively by at least about 10% when compared to a volumetric flow to a compressor in an otherwise similar INRU system that has only a hydrocarbon membrane unit; wherein the first cooling unit is configured to receive at least a portion of the compressed gas stream prior to introducing at least a portion of the compressed gas stream to the first separation unit; wherein the first separation unit is a vapor-liquid separator configured to receive at least a portion of the compressed gas stream, and to produce a first hydrocarbon stream and a nitrogen membrane unit feed stream, wherein the first hydrocarbon stream is a liquid stream, and wherein the nitrogen membrane unit feed stream is a gaseous stream; wherein the first stripping unit is configured to receive at least a portion of the first hydrocarbon stream, and to produce a purified first hydrocarbon stream and a third nitrogen stream; wherein the nitrogen membrane unit is configured to receive at least a portion of the nitrogen membrane unit feed stream, and to produce a first nitrogen stream and a retentate stream, wherein the nitrogen membrane unit has a nitrogen selective membrane disposed therein, wherein the nitrogen selective membrane allows nitrogen to pass through and be collected as a permeate stream (e.g., first nitrogen stream), wherein the nitrogen selective membrane does not allow hydrocarbons to pass through (although some lighter hydrocarbons could permeate through the nitrogen selective membrane, and as such at least a portion of the first nitrogen stream can be recycled back to the INRU compressor to recover such lighter hydrocarbons that could permeate through the nitrogen selective membrane), wherein hydrocarbons can be collected as the retentate stream, wherein the first nitrogen stream has a pressure of from about 1 psig to about 50 psig, wherein the nitrogen recycle stream comprises at least a portion of the first nitrogen stream, and wherein the retentate stream has a hydrocarbon dew point that is greater than a hydrocarbon dew point of the membrane unit feed stream; wherein the second cooling unit is configured to receive at least a portion of the retentate stream prior to introducing at least a portion of the retentate stream to the second separation unit; wherein the second separation unit is a vapor-liquid separator configured to receive at least a portion of the retentate stream, and to produce a second hydrocarbon stream and a hydrocarbon membrane unit feed stream, wherein the second hydrocarbon stream is a liquid stream, wherein the hydrocarbon membrane unit feed stream is a gaseous stream, and wherein the hydrocarbon membrane unit feed stream comprises hydrocarbons and nitrogen; wherein the second stripping unit is configured to receive at least a portion of the second hydrocarbon stream, and to produce a purified second hydrocarbon stream and a fourth nitrogen stream; and wherein the hydrocarbon membrane unit is configured to receive at least a portion of the hydrocarbon membrane unit feed stream, and to produce a fifth nitrogen stream (e.g., purified nitrogen stream) and a third hydrocarbon stream, wherein the hydrocarbon membrane unit has a hydrocarbon selective membrane disposed therein, wherein the hydrocarbon selective membrane allows hydrocarbons to pass through and be collected as a permeate stream (e.g., third hydrocarbon stream, which can be recycled back to the INRU compressor), wherein the hydrocarbon selective membrane does not allow nitrogen to pass through (although nitrogen could permeate through the hydrocarbon selective membrane, and as such at least a portion of the third hydrocarbon stream can be recycled back to the INRU compressor to recover such nitrogen that could permeate through the hydrocarbon selective membrane), and wherein nitrogen can be collected as a retentate stream (e.g., purified nitrogen stream, purified nitrogen stream). As will be appreciated by one of skill in the art, and with the help of this disclosure, some nitrogen and light gas can permeate through the hydrocarbon selective membrane. In some configurations of the INRU system disclosed herein, the first nitrogen stream can be combined with the fifth nitrogen stream (e.g., high purity nitrogen) from the hydrocarbon membrane unit to form a medium purity nitrogen purge gas stream. The medium purity nitrogen purge gas stream could be further recycled to a purge vessel, such as the purge vessel 400, for example via the purge gas stream 410 (e.g., via the recycle stream 509 as shown in FIG. 1A).

One or more of the disclosed systems (e.g., PEP system 1000), processes (e.g., PEP process 2000), or both can advantageously display improvements in one or more system characteristics, process characteristics, or both when compared to otherwise similar systems, processes, or both lacking an INRU comprising both a membrane unit and a PSA unit. In an aspect, the INRU as disclosed herein can advantageously allow for the use of a smaller PSA unit, when compared to an otherwise similar INRU that has either a membrane unit or a PSA unit but not both.

The INRU (e.g., INRU 500 or 501) as disclosed herein can advantageously allow for a decreased volumetric flow to the INRU compressor, when compared to an otherwise similar INRU that has either a membrane unit or a PSA unit but not both. The main cost driver (e.g., INRU compressor size and throughput) for the INRU system can be reduced. The PSA unit size can be reduced due to the reduced PSA feed stream. Capital cost associated with the PSA unit can therefore be reduced. Additional advantages of the systems, processes, or both for the production of a polyethylene polymer as disclosed herein can be apparent to one of skill in the art viewing this disclosure.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

EXAMPLES

The disclosure having been generally described, the following examples are given as particular embodiments of the disclosure and to demonstrate the practice and advantages thereof. It is understood that the examples are given by way of illustration and are not intended to limit the specification of the claims to follow in any manner.

EXAMPLE 1

The performance of various INRU systems was studied as follows. Case #1 was studied for an INRU comprising a PSA unit only, without a nitrogen membrane unit. Cases #2, #3, and #4 were studied for an INRU comprising both a PSA unit and a nitrogen membrane unit, such as the INRU of FIG. 1B. For case #2, 30% of nitrogen of the stream fed to the nitrogen membrane unit was recovered in the retentate stream (e.g., comprising hydrocarbons), and 65% of the nitrogen recovered from the nitrogen membrane unit was recycled back to the INRU compressor. For case #3, 10% of nitrogen of the stream fed to the nitrogen membrane unit was recovered in the retentate stream (e.g., comprising hydrocarbons), and 65% of the nitrogen recovered from the nitrogen membrane unit was recycled back to the INRU compressor. For case #4, 30% of nitrogen of the stream fed to the nitrogen membrane unit was recovered in the retentate stream (e.g., comprising hydrocarbons), and 100% of the nitrogen recovered from the nitrogen membrane unit was recycled back to the INRU compressor. The data for cases #1, #2, #3, and #4 are displayed in Table 1. The INRU compressor used for these experiments was a two-stage screw compressor, manufactured by Mycom (model#3225 LSC). The INRU compressor was rated for the suction flow of 200,940 ft³/hr, at a temperature of about 94° F. and at a pressure of about 18 psia. Compressor discharge pressure was rated for 248 psia. PSA feed stream temperature was 50° F. Adsorption step pressure was 235 psia and purge step pressure was 20 psia. The recovered nitrogen was the nitrogen stream recovered from the PSA unit.

TABLE 1

| Flow Rate (lbs/hr) | Case #1 Base Case: PSA Only | Case #2 PSA with N₂ Mem (30% N₂ Permeation) 65% N₂ recycle | Case #3 PSA with N₂ Mem (10% N₂ Permeation) 65% N₂ recycle | Case #4 PSA with N₂ Mem (30% N₂ Permeation) 100% N₂ recycle |
|---|---|---|---|---|
| C₂ = + C₂ | 2299 | 908 | 972 | 1182 |
| IC₄ | 1675 | 965 | 1109 | 1266 |
| N₂ | 2359 | 1717 | 2032 | 2179 |
| Total PSA Feed | 6400 | 3620 | 4147 | 4676 |
| Tail Gas Flow | 4995 | 2604 | 2945 | 3381 |
| N₂ Recycle from Membrane Unit to Compressor | N/A | 594 | 254 | 1239 |
| Other Recycles to Compressor | 5831 | N/A | N/A | N/A |
| INRU Feed | 16878 | 16878 | 16878 | 16878 |
| Compressor Suction Flow | 27704 | 20076 | 20077 | 21498 |
| Compressor Suction Flow (ft³/hr) | 183354 | 138067 | 136928 | 159509 |
| Overall HC Recovery | 99.9% | 99.7% | 99.6% | 99.9% |
| N₂ Recovery | 1392 (59%) | 1013 (59%) | 1199 (59%) | 1286 (59%) |
| N₂ Purity (wt. %) | 99.1% | 99.7% | 99.7% | 99.2% |

IC₄ = isobutane.

It can be seen from Table 1 that all three new INRU processes (e.g., cases #2, #3, and #4) show reduced PSA feed and INRU compressor flow. This can translate to a potentially increased INRU feed and an extended PSA operation cycle time. As will be appreciated by one of skill in the art, and with the help of this disclosure, membrane performance is dependent upon the operation conditions, such as transmembrane pressure difference, temperature, and feed compositions. The cases displayed in Table 1 were not necessarily run with optimal parameters for an INRU comprising both a PSA unit and a membrane unit, the experiments were run as a proof of concept. The low pressure nitrogen rich stream (5 psig in these cases) that is not recycled back to the INRU compressor can be used as a medium purity nitrogen purge in a purge vessel upstream of the INRU in a PEP process. Depending on the extent of nitrogen permeation through the nitrogen selective membrane, there might be a need for a process heater to heat the membrane feed, or alternatively to heat the retentate stream within the membrane. Such heating can be employed to ensure that hydrocarbon condensation within the membrane unit can be prevented. In addition, pending upon the existing capacities of a purification section downstream of the INRU, there may be a need for a nitrogen stripper to control the nitrogen content in the recovered hydrocarbon stream (e.g., first HC stream and second HC stream in FIG. 1B), as such nitrogen content is slightly higher than that in the base case. Hydrocarbon recovery rate is almost identical between the base case wherein the INRU comprises a PSA unit only; and an INRU comprising both a PSA unit and a membrane unit. In all PSA cases, 41% nitrogen in the PSA feed was used as the purge gas stream for the simplicity of analysis. The tail gas stream from the PSA unit contained recovered hydrocarbons and nitrogen purge gas. In the base case (case #1), 41% of the PSA nitrogen product was used to purge desorbed hydrocarbons during the purge step. It is expected less nitrogen will be used for purging for PSA cases, due to the reduced hydrocarbon feed. In the hybrid cases (cases #2, #3, and #4), since hydrocarbons and nitrogen in the PSA feed were much reduced, the tail gas stream flow was significantly reduced.

EXAMPLE 2

The performance of various INRU systems was studied as follows. Case #5 was studied for an INRU comprising a nitrogen membrane unit only, without a PSA unit. Case #6 was studied for an INRU comprising a PSA unit only, without a nitrogen membrane unit. Case #7 was studied for an INRU comprising both a PSA unit and a nitrogen membrane unit, such as the INRU of FIG. 1B. For case #7, 30% of nitrogen of the stream fed to the nitrogen membrane unit was recovered in the retentate stream (e.g., comprising hydrocarbons), and 65% of the nitrogen recovered from the nitrogen membrane unit was recycled back to the INRU compressor. The data for cases #5, #6, and #7 are displayed in Table 1. The INRU compressor used for these experiments was a two-stage screw compressor, manufactured by Mycom (model#4032 LM). The INRU compressor was rated for the suction flow of 297,000 ft³/hr, at a temperature of about 100° F. and at a pressure of about 16 psia. Compressor discharge pressure was rated for 345 psia. PSA feed stream temperature was 50° F. Adsorption step pressure was 235 psia and purge step pressure was 20 psia. The recovered nitrogen was the nitrogen stream recovered from the PSA unit.

TABLE 2

| Flow Rate (lbs/hr) | Case #5 Membrane Only Process | Case #6 PSA Only Process | Case #7 PSA with N₂ Mem (30% N₂ Permeation) 65% N₂ recycle |
|---|---|---|---|
| C₂ = + C₂ | N/A | 4068 | 1528 |
| IC₄ | | 3183 | 1928 |
| N₂ | | 4665 | 3509 |
| Total PSA Feed | | 12009 | 7036 |
| Tail/Permeate Gas Flow | 21980 | 9233 | 4947 |
| N₂ Recycle from Membrane Unit to Compressor | N/A | N/A | 1198 |
| Other Recycles to Compressor | | 5980 | N/A |
| INRU Feed | 20213 | 20213 | 20213 |
| Compressor Suction Flow | 42193 | 35426 | 26358 |
| Compressor Suction Flow (ft³/hr) | 255904 | 268500 | 201972 |
| Compressor Outlet pressure (psia) | 340 | 235 | 235 |
| HC Recovery | 99.8% | 99.9% | 99.3% |
| N₂ Recovery | 2442 (28%) | 2752 (59%) | 2070 (59%) |
| N₂ Purity (wt %) | 98.3% | 99.1% | 99.1% |

IC₄ = isobutane.

The data in Table 2 indicates that for the INRU comprising both a PSA unit and a membrane unit, over a 20% reduction of compressor flow as well as reduced outlet pressure was observed. Such compressor flow reduction could have significant capital savings. The hydrocarbon and nitrogen recovery are similar for case #7 (INRU comprising both a PSA unit and a membrane unit), when compared with cases #5 and #6.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

ADDITIONAL DISCLOSURE

The following enumerated embodiments are provided as nonlimiting examples.

A first aspect which is a process for component separation in a polymer production system, comprising: (a) separating a polymerization product stream into a gas stream and a polymer stream, wherein the polymer stream comprises polyethylene, isobutane, ethylene and ethane; (b) contacting at least a portion of the polymer stream with a purge gas in a purge vessel to yield a purged polymer stream and a spent purge gas stream, wherein the purged polymer stream comprises polyethylene, and wherein the spent purge gas stream comprises purge gas, isobutane, ethylene, and ethane; (c) introducing at least a portion of the spent purge gas stream to a compressor to produce a compressed gas stream; (d) introducing at least a portion of the compressed gas stream to a first separation unit to produce a first hydrocarbon stream and a membrane unit feed stream, wherein the first hydrocarbon stream comprises equal to or greater than about 50% of the isobutane of the compressed gas stream, and wherein the membrane unit feed stream comprises equal to or greater than about 95% of the purge gas of the compressed gas stream; (e) introducing at least a portion of the membrane unit feed stream to a membrane unit to produce a first recovered purge gas stream and a retentate stream, wherein the retentate stream comprises less than about 30% of the purge gas of the membrane unit feed stream; (f) introducing at least a portion of the retentate stream to a second separation unit to produce a second hydrocarbon stream and a pressure swing adsorption (PSA) unit feed stream, wherein the PSA unit feed stream comprises equal to or greater than about 97% of the purge gas of the retentate stream; and (g) introducing at least a portion of the PSA unit feed stream to a PSA unit to produce a second recovered purge gas stream and a tail gas stream, wherein a molar concentration of purge gas in the second recovered purge gas stream is greater than a molar concentration of purge gas in the first recovered purge gas stream.

A second aspect which is the process of the first aspect further comprising (i) recycling at least a portion of the first recovered purge gas stream to the compressor; and (ii) recycling at least a portion of the tail gas stream to the compressor.

A third aspect which is the process of the second aspect, wherein the compressor has a volumetric flow that is reduced by at least about 20% when compared to a volumetric flow to a compressor in an otherwise similar polymer production system that has either a membrane unit or a PSA unit but not both.

A fourth aspect which is the process of any one of the first through the third aspects, wherein the compressed gas stream is cooled prior to the step (d) of introducing at least a portion of the compressed gas stream to a first separation unit.

A fifth aspect which is the process of any one of the first through the fourth aspects, wherein the retentate stream is cooled prior to the step (f) of introducing at least a portion of the retentate stream to a second separation unit.

A sixth aspect which is the process of any one of the first through the fifth aspects, wherein at least a portion of the first hydrocarbon stream is introduced to a first stripping unit to produce a purified first hydrocarbon stream and a third recovered purge gas stream, wherein an amount of purge gas in the purified first hydrocarbon stream is lower than an amount of purge gas in the first hydrocarbon stream.

A seventh aspect which is the process of any one of the first through the sixth aspects, wherein at least a portion of the second hydrocarbon stream is introduced to a second stripping unit to produce a purified second hydrocarbon stream and a fourth recovered purge gas stream, wherein an amount of purge gas in the purified second hydrocarbon stream is lower than an amount of purge gas in the second hydrocarbon stream.

An eighth aspect which is the process of any one of the first through the seventh aspects, wherein the first recovered purge gas stream has a pressure of from about 1 psig to about 50 psig.

A ninth aspect which is the process of any one of the first through the eighth aspects, wherein at least a portion of the membrane unit feed stream is heated prior to the step (e) of introducing at least a portion of the membrane unit feed stream to a membrane unit.

A tenth aspect which is the process of any one of the first through the ninth aspects, wherein the membrane unit is heated.

An eleventh aspect which is the process of any one of the first through the tenth aspects, wherein the retentate stream has a hydrocarbon dew point that is greater than a hydrocarbon dew point of the membrane unit feed stream.

A twelfth aspect which is the process of any one of the first through the eleventh aspects, wherein the PSA unit is characterized by a cycle time of from about 1 minute to about 60 minutes.

A thirteenth aspect which is the process of any one of the first through the twelfth aspects, wherein the PSA unit is characterized by a cycle time that is increased by at least about 50% when compared to a cycle time of a PSA unit in an otherwise similar polymer production system that lacks a membrane unit.

A fourteenth aspect which is the process of any one of the first through the thirteenth aspects, wherein from about 2 to about 8 PSA units are operated in parallel.

A fifteenth aspect which is the process of any one of the first through the fourteenth aspects further comprising recycling a portion of the first recovered purge gas stream to the purge vessel.

A sixteenth aspect which is the process of any one of the first through the fifteenth aspects, wherein at least a portion of the gas stream is introduced to one or more distillation columns to produce isobutane.

A seventeenth aspect which is the process of the sixteenth aspect, wherein at least a portion of the first hydrocarbon stream, at least a portion of the second hydrocarbon stream, or both are recycled to the one or more distillation columns.

An eighteenth aspect which is the process of any one of the first through the seventeenth aspects, wherein at least a portion of the first hydrocarbon stream is introduced to a first stripping unit to produce a purified first hydrocarbon stream and a third recovered purge gas stream; wherein at least a portion of the second hydrocarbon stream is introduced to a second stripping unit to produce a purified second hydrocarbon stream and a fourth recovered purge gas stream; and wherein at least a portion of the first hydrocarbon stream, at least a portion of the purified first hydrocarbon stream, at least a portion of the second hydrocarbon stream, at least a portion of the purified second hydrocarbon stream, or combinations thereof are recycled to the one or more distillation columns.

A nineteenth aspect which is the process of any one of the first through the eighteenth aspects, wherein at least a portion of the isobutane is introduced to the PSA unit as a sweeping gas to produce the tail gas stream, and wherein an amount of isobutane in the tail gas stream is greater than an amount of isobutane in the PSA unit feed stream.

A twentieth aspect which is the process of any one of the first through the nineteenth aspects, wherein the PSA unit feed stream is reduced by at least about 40% when compared to a PSA unit feed stream in an otherwise similar polymer production system that lacks a membrane unit.

A twenty-first aspect which is the process of any one of the first through the twentieth aspects, wherein the compressor is characterized by a compressor power that is reduced by at least about 10% when compared to a compressor power of a compressor in an otherwise similar polymer production system that has either a membrane unit or a PSA unit but not both.

A twenty-second aspect which is the process of any one of the first through the twenty-first aspects further comprising recycling at least a portion of the second recovered purge gas stream to the purge vessel.

A twenty-third aspect which is a process for component separation in a polymer production system, comprising: (a) separating a polymerization product stream into a gas stream and a polymer stream, wherein the polymer stream comprises polyethylene, isobutane, ethylene and ethane, and wherein the gas stream comprises ethylene, ethane, and isobutane; (b) contacting at least a portion of the polymer stream with a nitrogen stream in a purge vessel to yield a purged polymer stream and a spent nitrogen stream, wherein the purged polymer stream comprises polyethylene, and wherein the spent nitrogen comprises nitrogen, isobutane, ethylene, and ethane; (c) introducing at least a portion of the spent nitrogen stream to a compressor to produce a compressed gas stream; (d) introducing at least a portion of the compressed gas stream to a first separation unit to produce a first hydrocarbon stream and a membrane unit feed stream, wherein the first hydrocarbon stream comprises equal to or greater than about 50% of the isobutane of the compressed gas stream, and wherein the membrane unit feed stream comprises equal to or greater than about 95% of the nitrogen of the compressed gas stream; (e) introducing at least a portion of the membrane unit feed stream to a nitrogen membrane unit to produce a first recovered nitrogen stream and a retentate stream, wherein the retentate stream comprises less than about 30% of the nitrogen of the membrane unit feed stream; (f) recycling a first portion of the first recovered nitrogen stream to the compressor and recycling a second portion of the first recovered nitrogen stream to the purge vessel; (g) introducing at least a portion of the retentate stream to a second separation unit to produce a second hydrocarbon stream and a pressure swing adsorption (PSA) unit feed stream, wherein the PSA unit feed stream comprises equal to or greater than about 97% of the nitrogen of the retentate stream; (h) introducing at least a portion of the PSA unit feed stream to a PSA unit to produce a second recovered nitrogen stream and a tail gas stream, wherein a molar concentration of nitrogen in the second recovered nitrogen stream is greater than a molar concentration of nitrogen in the first recovered nitrogen stream; and (i) recycling at least a portion of the tail gas stream to the compressor.

A twenty-fourth aspect which is the process of the twenty-third aspect, wherein the compressor has a volumetric flow that is reduced by at least about 20% when compared to a volumetric flow to a compressor in an otherwise similar polymer production system that has either a nitrogen membrane unit or a PSA unit but not both.

A twenty-fifth aspect, which is the process of any one of the twenty-third and the twenty-fourth aspects further comprising (i) cooling at least a portion of the compressed gas stream prior to the step (d) of introducing at least a portion of the compressed gas stream to a first separation unit; and (ii) cooling at least a portion of the retentate stream prior to the step (g) of introducing at least a portion of the retentate stream to a second separation unit.

A twenty-sixth aspect which is an isobutane and nitrogen recovery unit (INRU) system comprising a compressor, a first separation unit, a nitrogen membrane unit, a second separation unit and a pressure swing adsorption (PSA) unit; wherein the compressor is configured to receive a spent purge gas stream, a nitrogen recycle stream, and a tail gas stream, and to produce a compressed gas stream; wherein the compressor has a volumetric flow that is reduced by at least about 20% when compared to a volumetric flow to a compressor in an otherwise similar INRU system that has either a membrane unit or a PSA unit but not both; wherein the first separation unit is a vapor-liquid separator configured to receive at least a portion of the compressed gas stream, and to produce a first hydrocarbon stream and a membrane unit feed stream, wherein the first hydrocarbon stream is a liquid stream, and wherein the membrane unit feed stream is a gaseous stream; wherein the nitrogen membrane unit is configured to receive at least a portion of the membrane unit feed stream, and to produce a first nitrogen stream and a retentate stream, wherein the first nitrogen stream has a pressure of from about 1 psig to about 50 psig, wherein the nitrogen recycle stream comprises at least a portion of the first nitrogen stream, and wherein the retentate stream has a hydrocarbon dew point that is greater than a hydrocarbon dew point of the membrane unit feed stream; wherein the second separation unit is a vapor-liquid separator configured to receive at least a portion of the retentate stream, and to produce a second hydrocarbon stream and a PSA unit feed stream, wherein the second hydrocarbon stream is a liquid stream, wherein the PSA unit feed stream is a gaseous stream, and wherein the PSA unit feed stream comprises hydrocarbons and nitrogen; and wherein the PSA unit is configured to receive at least a portion of the PSA unit feed stream, and to produce a second nitrogen stream and the tail gas stream, wherein the PSA unit has a PSA adsorber disposed therein, wherein the PSA adsorber allows the nitrogen to pass through the PSA unit and be collected as the second nitrogen stream, wherein the PSA adsorber adsorbs the hydrocarbons, and wherein a sweeping gas stream comprising isobutane desorbs the hydrocarbons from the PSA adsorber to produce the tail gas stream.

A twenty-seventh aspect which is the INRU system of the twenty-sixth aspect further comprising a first cooling unit, wherein the first cooling unit is configured to receive at least a portion of the compressed gas stream prior to introducing at least a portion of the compressed gas stream to the first separation unit; and a second cooling unit, wherein the second cooling unit is configured to receive at least a portion of the retentate stream prior to introducing at least a portion of the retentate stream to the second separation unit.

A twenty-eighth aspect which is the INRU system of any one of the twenty-sixth and the twenty-seventh aspects further comprising a first stripping unit, wherein the first stripping unit is configured to receive at least a portion of the first hydrocarbon stream, and to produce a purified first hydrocarbon stream and a third nitrogen stream; and a second stripping unit, wherein the second stripping unit is configured to receive at least a portion of the second hydrocarbon stream, and to produce a purified second hydrocarbon stream and a fourth nitrogen stream.

A twenty-ninth aspect which is a process for ethylene polymerization, comprising: (a) polymerizing ethylene in a loop slurry reactor system to obtain a polymerization product stream; (b) separating at least a portion of the polymerization product stream in a flash chamber into a gas stream and a polymer stream comprising polyethylene, isobutane, ethylene and ethane; (c) contacting at least a portion of the polymer stream with nitrogen in a purge vessel to yield a purged polymer stream and a spent nitrogen stream, wherein the purged polymer stream comprises polyethylene, and wherein the spent nitrogen comprises nitrogen, isobutane, ethylene, and ethane; (d) introducing at least a portion of the spent nitrogen stream to a compressor to produce a compressed gas stream; (e) introducing at least a portion of the compressed gas stream to a first separation unit to produce a first hydrocarbon stream and a membrane unit feed stream, wherein the first hydrocarbon stream comprises equal to or greater than about 50% of the isobutane of the compressed gas stream, and wherein the membrane unit feed stream comprises equal to or greater than about 95% of the nitrogen of the compressed gas stream; (f) introducing at least a portion of the membrane unit feed stream to a nitrogen membrane unit to produce a first recovered nitrogen stream and a retentate stream, wherein the retentate stream comprises less than about 30% of the nitrogen of the membrane unit feed stream; (g) recycling a first portion of the first recovered nitrogen stream to the compressor; (h) recycling a second portion of the first recovered nitrogen stream to the purge vessel; (i) introducing at least a portion of the retentate stream to a second separation unit to produce a second hydrocarbon stream and a pressure swing adsorption (PSA) unit feed stream, wherein the PSA unit feed stream comprises equal to or greater than about 97% of the nitrogen of the retentate stream; (j) introducing at least a portion of the PSA unit feed stream to a PSA unit to produce a second recovered nitrogen stream and a tail gas stream, wherein a molar concentration of nitrogen in the second recovered nitrogen stream is greater than a molar concentration of nitrogen in the first recovered nitrogen stream; and (k) recycling at least a portion of the tail gas stream to the compressor.

A thirtieth aspect which is the process of the twenty-ninth aspect, wherein the compressor has a volumetric flow that is reduced by at least about 20% when compared to a volumetric flow to a compressor in an otherwise similar polymer production system that has either a membrane unit or a PSA unit but not both.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, and the like; greater than 0.10 includes 0.11, 0.12, 0.13, and the like). For example, whenever a numerical range with a lower limit, $R_1$, and an upper limit, $R_u$, is disclosed, any number falling within the range is specifically disclosed. In particular, the following numbers within the range are specifically disclosed: $R=R_1+k*(R_u-R_1)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

We claim:

1. A process for component separation in a polymer production system, comprising:
   (a) separating a polymerization product stream into a gas stream and a polymer stream, wherein the polymer stream comprises polyethylene, isobutane, ethylene and ethane;
   (b) contacting at least a portion of the polymer stream with a purge gas in a purge vessel to yield a purged polymer stream and a spent purge gas stream, wherein the purged polymer stream comprises polyethylene, and wherein the spent purge gas stream comprises purge gas, isobutane, ethylene, and ethane;
   (c) introducing at least a portion of the spent purge gas stream to a compressor to produce a compressed gas stream;
   (d) introducing at least a portion of the compressed gas stream to a first separation unit to produce a first hydrocarbon stream and a membrane unit feed stream, wherein the first hydrocarbon stream comprises equal to or greater than about 50% of the isobutane of the compressed gas stream, and wherein the membrane unit feed stream comprises equal to or greater than about 95% of the purge gas of the compressed gas stream;

(e) introducing at least a portion of the membrane unit feed stream to a membrane unit to produce a first recovered purge gas stream and a retentate stream, wherein the retentate stream comprises less than about 30% of the purge gas of the membrane unit feed stream;

(f) introducing at least a portion of the retentate stream to a second separation unit to produce a second hydrocarbon stream and a pressure swing adsorption (PSA) unit feed stream, wherein the PSA unit feed stream comprises equal to or greater than about 97% of the purge gas of the retentate stream; and (g) introducing at least a portion of the PSA unit feed stream to a PSA unit to produce a second recovered purge gas stream and a tail gas stream, wherein a molar concentration of purge gas in the second recovered purge gas stream is greater than a molar concentration of purge gas in the first recovered purge gas stream.

2. The process of claim 1 further comprising (i) recycling at least a portion of the first recovered purge gas stream to the compressor; and (ii) recycling at least a portion of the tail gas stream to the compressor.

3. The process of claim 2, wherein the compressor has a volumetric flow that is reduced by at least about 20% when compared to a volumetric flow to a compressor in an otherwise similar polymer production system that has either a membrane unit or a PSA unit but not both.

4. The process of claim 1, wherein at least a portion of the first hydrocarbon stream is introduced to a first stripping unit to produce a purified first hydrocarbon stream and a third recovered purge gas stream, wherein an amount of purge gas in the purified first hydrocarbon stream is lower than an amount of purge gas in the first hydrocarbon stream.

5. The process of claim 1, wherein at least a portion of the second hydrocarbon stream is introduced to a second stripping unit to produce a purified second hydrocarbon stream and a fourth recovered purge gas stream, wherein an amount of purge gas in the purified second hydrocarbon stream is lower than an amount of purge gas in the second hydrocarbon stream.

6. The process of claim 1, wherein the first recovered purge gas stream has a pressure of from about 1 psig to about 50 psig.

7. The process of claim 1, wherein at least a portion of the membrane unit feed stream is heated prior to the step (e) of introducing at least a portion of the membrane unit feed stream to a membrane unit; wherein the membrane unit is heated; or both.

8. The process of claim 1, wherein the retentate stream has a hydrocarbon dew point that is greater than a hydrocarbon dew point of the membrane unit feed stream.

9. The process of claim 1, wherein the PSA unit is characterized by a cycle time that is increased by at least about 50% when compared to a cycle time of a PSA unit in an otherwise similar polymer production system that lacks a membrane unit.

10. The process of claim 1 further comprising recycling a portion of the first recovered purge gas stream to the purge vessel.

11. The process of claim 1, wherein at least a portion of the gas stream is introduced to one or more distillation columns to produce isobutane.

12. The process of claim 11, wherein at least a portion of the first hydrocarbon stream, at least a portion of the second hydrocarbon stream, or both are recycled to the one or more distillation columns.

13. The process of claim 11, wherein at least a portion of the first hydrocarbon stream is introduced to a first stripping unit to produce a purified first hydrocarbon stream and a third recovered purge gas stream; wherein at least a portion of the second hydrocarbon stream is introduced to a second stripping unit to produce a purified second hydrocarbon stream and a fourth recovered purge gas stream; and wherein at least a portion of the first hydrocarbon stream, at least a portion of the purified first hydrocarbon stream, at least a portion of the second hydrocarbon stream, at least a portion of the purified second hydrocarbon stream, or combinations thereof are recycled to the one or more distillation columns.

14. The process of claim 11, wherein at least a portion of the isobutane is introduced to the PSA unit as a sweeping gas to produce the tail gas stream, and wherein an amount of isobutane in the tail gas stream is greater than an amount of isobutane in the PSA unit feed stream.

15. The process of claim 1, wherein the PSA unit feed stream is reduced by at least about 40% when compared to a PSA unit feed stream in an otherwise similar polymer production system that lacks a membrane unit.

16. The process of claim 1, wherein the compressor is characterized by a compressor power that is reduced by at least about 10% when compared to a compressor power of a compressor in an otherwise similar polymer production system that has either a membrane unit or a PSA unit but not both.

17. The process of claim 1 further comprising recycling at least a portion of the second recovered purge gas stream to the purge vessel.

18. A process for component separation in a polymer production system, comprising:

(a) separating a polymerization product stream into a gas stream and a polymer stream, wherein the polymer stream comprises polyethylene, isobutane, ethylene and ethane, and wherein the gas stream comprises ethylene, ethane, and isobutane;

(b) contacting at least a portion of the polymer stream with a nitrogen stream in a purge vessel to yield a purged polymer stream and a spent nitrogen stream, wherein the purged polymer stream comprises polyethylene, and wherein the spent nitrogen comprises nitrogen, isobutane, ethylene, and ethane;

(c) introducing at least a portion of the spent nitrogen stream to a compressor to produce a compressed gas stream;

(d) introducing at least a portion of the compressed gas stream to a first separation unit to produce a first hydrocarbon stream and a membrane unit feed stream, wherein the first hydrocarbon stream comprises equal to or greater than about 50% of the isobutane of the compressed gas stream, and wherein the membrane unit feed stream comprises equal to or greater than about 95% of the nitrogen of the compressed gas stream;

(e) introducing at least a portion of the membrane unit feed stream to a nitrogen membrane unit to produce a first recovered nitrogen stream and a retentate stream, wherein the retentate stream comprises less than about 30% of the nitrogen of the membrane unit feed stream;

(f) recycling a first portion of the first recovered nitrogen stream to the compressor and recycling a second portion of the first recovered nitrogen stream to the purge vessel;

(g) introducing at least a portion of the retentate stream to a second separation unit to produce a second hydrocarbon stream and a pressure swing adsorption (PSA) unit feed stream, wherein the PSA unit feed stream comprises equal to or greater than about 97% of the nitrogen of the retentate stream;

(h) introducing at least a portion of the PSA unit feed stream to a PSA unit to produce a second recovered nitrogen stream and a tail gas stream, wherein a molar concentration of nitrogen in the second recovered nitrogen stream is greater than a molar concentration of nitrogen in the first recovered nitrogen stream; and (i) recycling at least a portion of the tail gas stream to the compressor.

19. The process of claim 18, wherein the compressor has a volumetric flow that is reduced by at least about 20% when compared to a volumetric flow to a compressor in an otherwise similar polymer production system that has either a nitrogen membrane unit or a PSA unit but not both.

20. A process for ethylene polymerization, comprising:

(a) polymerizing ethylene in a loop slurry reactor system to obtain a polymerization product stream;

(b) separating at least a portion of the polymerization product stream in a flash chamber into a gas stream and a polymer stream comprising polyethylene, isobutane, ethylene and ethane;

(c) contacting at least a portion of the polymer stream with nitrogen in a purge vessel to yield a purged polymer stream and a spent nitrogen stream, wherein the purged polymer stream comprises polyethylene, and wherein the spent nitrogen comprises nitrogen, isobutane, ethylene, and ethane;

(d) introducing at least a portion of the spent nitrogen stream to a compressor to produce a compressed gas stream;

(e) introducing at least a portion of the compressed gas stream to a first separation unit to produce a first hydrocarbon stream and a membrane unit feed stream, wherein the first hydrocarbon stream comprises equal to or greater than about 50% of the isobutane of the compressed gas stream, and wherein the membrane unit feed stream comprises equal to or greater than about 95% of the nitrogen of the compressed gas stream;

(f) introducing at least a portion of the membrane unit feed stream to a nitrogen membrane unit to produce a first recovered nitrogen stream and a retentate stream, wherein the retentate stream comprises less than about 30% of the nitrogen of the membrane unit feed stream;

(g) recycling a first portion of the first recovered nitrogen stream to the compressor;

(h) recycling a second portion of the first recovered nitrogen stream to the purge vessel;

(i) introducing at least a portion of the retentate stream to a second separation unit to produce a second hydrocarbon stream and a pressure swing adsorption (PSA) unit feed stream, wherein the PSA unit feed stream comprises equal to or greater than about 97% of the nitrogen of the retentate stream;

(j) introducing at least a portion of the PSA unit feed stream to a PSA unit to produce a second recovered nitrogen stream and a tail gas stream, wherein a molar concentration of nitrogen in the second recovered nitrogen stream is greater than a molar concentration of nitrogen in the first recovered nitrogen stream; and (k) recycling at least a portion of the tail gas stream to the compressor.

21. The process of claim 20, wherein the compressor has a volumetric flow that is reduced by at least about 20% when compared to a volumetric flow to a compressor in an otherwise similar polymer production system that has either a membrane unit or a PSA unit but not both.

\* \* \* \* \*